US009981021B1

(12) United States Patent
Cao et al.

(10) Patent No.: US 9,981,021 B1
(45) Date of Patent: May 29, 2018

(54) SUBCUTANEOUS THERAPEUTIC ENZYME FORMULATIONS, USES, AND METHODS FOR GENERATING THEREOF

(71) Applicant: KINETIQ, INC., Claremont, CA (US)

(72) Inventors: Mingju Cao, Pomona, CA (US); Alexander M. Cao, Pomona, CA (US)

(73) Assignee: KINETIQ, INC., Claremont, CA (US)

( * ) Notice: Subject to any disclaimer, the term of this patent is extended or adjusted under 35 U.S.C. 154(b) by 0 days. days.

(21) Appl. No.: 15/093,613

(22) Filed: Apr. 7, 2016

Related U.S. Application Data

(60) Provisional application No. 62/145,424, filed on Apr. 9, 2015.

(51) Int. Cl.
*A61K 38/05* (2006.01)
*A61K 38/47* (2006.01)
*A61K 9/00* (2006.01)

(52) U.S. Cl.
CPC ............ *A61K 38/47* (2013.01); *A61K 9/0019* (2013.01); *C12Y 302/01022* (2013.01); *C12Y 302/01035* (2013.01)

(58) Field of Classification Search
CPC ............................ C12N 9/2465; C12N 9/2474
See application file for complete search history.

(56) References Cited

U.S. PATENT DOCUMENTS

| | | | |
|---|---|---|---|
| 5,356,804 A | 10/1994 | Desnick et al. | |
| 5,401,650 A | 3/1995 | Desnick et al. | |
| 5,549,892 A | 8/1996 | Friedman et al. | |
| 6,066,626 A | 5/2000 | Yew et al. | |
| 6,083,725 A | 7/2000 | Selden et al. | |
| 6,210,666 B1 | 4/2001 | Miyamura | |
| 6,395,884 B1 | 5/2002 | Selden et al. | |
| 6,451,600 B1 | 9/2002 | Rasmussen et al. | |
| 6,458,574 B1 | 10/2002 | Selden et al. | |
| 7,011,831 B2 | 3/2006 | Calhoun et al. | |
| 7,348,000 B2 | 3/2008 | Dwek et al. | |
| 7,446,098 B2 | 11/2008 | Fan | |
| 7,740,861 B2 | 6/2010 | Ostroff | |
| 7,785,856 B2 | 8/2010 | Lebowitz et al. | |
| 7,807,618 B2 | 10/2010 | Matalon | |
| 7,829,081 B2 | 11/2010 | Bookbinder et al. | |
| 7,833,742 B2 | 11/2010 | Treco et al. | |
| 7,935,336 B2 | 5/2011 | Sakuraba et al. | |
| 8,318,154 B2* | 11/2012 | Frost ..................... | A61K 38/28 424/94.61 |
| 8,323,640 B2 | 12/2012 | Sakuraba et al. | |
| 8,536,148 B2 | 9/2013 | Raben et al. | |
| 8,569,032 B2 | 10/2013 | Sakuraba et al. | |
| 8,580,275 B2 | 11/2013 | Ostroff | |
| 8,637,045 B2 | 1/2014 | Ginns et al. | |
| 8,668,907 B2 | 3/2014 | Sakuraba et al. | |
| 8,741,620 B2 | 6/2014 | Shaaltiel et al. | |
| 8,785,168 B2 | 7/2014 | Lebowitz et al. | |
| 2003/0215432 A1* | 11/2003 | Matalon ................. | A61K 38/46 424/94.61 |
| 2011/0076273 A1 | 3/2011 | Adler et al. | |
| 2011/0237538 A1 | 9/2011 | De Moor et al. | |
| 2012/0288489 A1* | 11/2012 | Wolf ...................... | A61K 38/46 424/94.61 |
| 2014/0037612 A1 | 2/2014 | Sturk et al. | |
| 2014/0050666 A1* | 2/2014 | Calhoun .................. | C12N 9/96 424/9.6 |
| 2014/0219988 A1 | 8/2014 | Sakuraba et al. | |

FOREIGN PATENT DOCUMENTS

| | | | |
|---|---|---|---|
| EP | 2405015 A3 | 3/2012 | |
| EP | 2674487 A3 | 2/2014 | |

OTHER PUBLICATIONS

Aldurazyme (Laronidase) Label Revised Apr. 2013.
Beck, M. Therapy for lysosomal storage disorders. IUBMB life, 62(1), 33-40 (2010).
Bookbinder, L. H., et al. A recombinant human enzyme for enhanced interstitial transport of therapeutics. Journal of Controlled Release, 114(2), 230-241 (2006).
Branton, M. H., et al. Natural history of Fabry renal disease: influence of α-galactosidase A activity and genetic mutations on clinical course. Medicine, 81(2), 122-138 (2002).
Bruni, S. et al. Update on treatment of lysosomal storage diseases. Acta Myologica XXVI; 87-92 (2007).
Cerezyme (imiglucerase for injection) Label last revised Dec. 2012.
Committee for Medicinal Products for Human Use (CHMP) Assessment Report—Herceptin (2013). Retrieved from: http://www.ema.europa.eu/docs/en_GB/document_library/EPAR_-_Assessment_Report_-_Variation/human/000278/WC500153233.pd.
Craig, A. S., et al. Ultrastructural organization of skin: classification on the basis of mechanical role. Connective Tissue Research, 16(3), 213-223 (1987).
Dunn, Amber L., et al., Hyaluranidase: a review of approved formulations, indications and off-label use in chronic pain management. Expert Opinion Biological Therapy 10(1):127-131 (2010).
Elaprase (idursulfase) Prescribing Information Label Last Revised Jun. 2013.
Fabrazyme (agalsidase beta) Prescribing Information Label Last Revised May 2010.
Fabry Registry. (2013). Annual Report 2013. Retrieved from: http://www.fabry.org/fsig.nsf/PDFs/PDFsR/$File/2013_Annual_Report.pd.
Germain, D. P. Fabry disease. Orphanet Journal of Rare Diseases, 5, 30 (2010).

(Continued)

*Primary Examiner* — Ruth A Davis

(74) *Attorney, Agent, or Firm* — The Roy Gross Law Firm, LLC; Roy Gross

(57) ABSTRACT

Provided herein are compositions containing a lysosomal storage disorder replacement enzyme (LSDRE) and a dispersing agent for subcutaneous injection for treatment of lysosomal storage diseases. Kits and methods of treatment are also provided.

20 Claims, 8 Drawing Sheets

(56) References Cited

OTHER PUBLICATIONS

Gokarn, Y. R., et al. Excipients for protein drugs. In A. Katdare & M. Chaubal (Eds.), Excipient development for pharmaceutical, biotechnology, and drug delivery systems (pp. 291-306). Boca Raton, FL: CRC Press (2006).
Goldstein, J. L., et al. The metabolic and molecular bases of inherited disease. Familial hypercholesterolemia. New York: McGraw-Hill, 2863-913 (2010).
Guce, Abigail I., et al. Catalytic Mechanism of Human-Galactosidase. The Journal of Biological Chemistry 285(6): 3625-3632 (Feb. 5, 2010).
Hwu, W. L., et al. Newborn screening for Fabry disease in Taiwan reveals a high incidence of the later-onset GLA mutation c. 936+919G A (IVS4+919G A). Human Mutation, 30(10), 1397-1405 (2009).
Jedrzejas, Mark J., et al. Structures of Vertebrate Hyaluronidases and Their Unique Enzymatic Mechanism of Hydrolysis. PROTEINS: Structure, Function, and Bioinformatics 61:227-238 (2005).
Lee, Karen et al. A biochemical and pharmacological comparison of enzyme replacement therapies for the glycolipid storage disorder Fabry disease. Glycobiology 13(4): 305-313 (2003).
Lumizyme® (alglucosidase alfa), for injection, for intravenous use Prescribing Information Last Revised Aug. 2014.
Mechtler, T. P., et al. Neonatal screening for lysosomal storage disorders: feasibility and incidence from a nationwide study in Austria. The Lancet, 379(9813), 335-341 (2012).
Meghdari, M., et al. Carboxyl-Terminal Truncations Alter the Activity of the Human α-Galactosidase A. PloS one, 10(2), e0118341 (2015).
Meikle, P. J., et al. Prevalence of lysosomal storage disorders. JAMA, 281(3), 249-254 (1999).
Myozyme® (alglucosidase alfa) Prescribing Information Label Last Revised May 2014.
Naglazyme (galsulfase) injection for intravenous use Prescribing Information Label Last Revised Mar. 2013.
Pisani, Antonio, et al., Agalsidase alfa and agalsidase beta in the treatment of Fabry disease: does the dose really matter? Genetics in Medicine 17(1); 21-23 (Jan. 2015).
Poppe, Leszek, et al. Three-Dimensional structure of the oligosaccharide terminus of globotriaosylceramide and isolglobotriaosylceramide in solution A rotating-frame NOE study using hydroxyl groups as long-range sensors in conformational analysis by 1H-NMR spectroscopy. Eur. J. Biochem 189: 313-325 (1990).
Porter, C. J., et al. Lymphatic transport of proteins after subcutaneous administration. Journal of pharmaceutical sciences, 89(3), 297-310 (2000).
Ratko, Thomas A., et al. Enzyme-Replacement Therapies for Lysosomal Storage Diseases. Effective Health Care Program Technical Brief No. 12. AHRQ Publication No. 12(13)-EHC154-EF. (Jan. 2013).

Replagal (alpha galactosidase) Prescribing Information Label Revised Mar. 8, 2006.
Richter, W. F., et al. Mechanistic determinants of biotherapeutics absorption following SC administration. The AAPS journal, 14(3), 559-570 (2012).
Ries, M., et al. Enzyme-replacement therapy with agalsidase alfa in children with Fabry disease. Pediatrics, 118(3), 924-932 (2006).
Schulze, C. M.D., et al. (Technical Report) Experimental Evaluation of Hyaluronidase Activity in Combination with Specific Drugs Applied in Clinical Techniques of Interventional Pain Management and Local Anaesthesia. Pain Physician 11:877-883 (2008).
Schulze, H., et al. Sphingolipids and lysosomal pathologies. Biochimica et Biophysica Acta (BBA)-Molecular and Cell Biology of Lipids, 1841(5), 799-810 (2014).
Shire, S. J., et al. Challenges in the development of high protein concentration formulations. Journal of pharmaceutical sciences, 93(6), 1390-1402 (2004).
Spada, M., et al. High incidence of later-onset Fabry disease revealed by newborn screening. The American Journal of Human Genetics, 79(1), 31-40 (2006).
Sweeley, C. C., & Klionsky, B. Fabry's disease: classification as a sphingolipidosis and partial characterization of a novel glycolipid. Journal of Biological Chemistry, 238(9), PC3148-PC3150 (1963).
Tajima, Youichi, et al. Use of a Modified a-N-Acetylgalactosaminidase in the Development of Enzyme Replacement Therapy for Fabry Disease. The American Journal of Human Genetics 85: 569-580 (Nov. 13, 2009).
Thomas, Jay R., et al. Assessing the Role of Human Recombinant Hyaluronidase in Gravity-Driven Subcutaneous Hydration: The INFUSE-LR Study.Journal of Palliative Medicine 10(6): 1312-1320 (2007).
Thomas, Philip, et al. HEK293 cell line: A vehicle for the expression of recombinant proteins. Journal of Pharmacological and Toxicological Methods 51: 187-200 (2005).
Vaughn, Daniel E. Accelerated Pharmacokinetics and Glucodynamics of Prandial Insulins Injected With Recombinant Human Hyaluronidase. Diabetes Technology & Therapeutics 11(6): 345-352 (2009.
VIMIZIM (elosulfase alfa) injection, for intravenous use prescribing information last revised Feb. 2014.
VITRASE® (hyaluronidase injection) Ovine, prescribing information last revised Oct. 2014.
VPRIV™ (velaglucerase alfa for injection) prescribing information last revised Feb. 2010.
Waldek, S., et al. Life expectancy and cause of death in males and females with Fabry disease: findings from the Fabry Registry. Genetics in Medicine, 11(11), 790-796 (2009).
Wasserman, R. L. Overview of recombinant human hyaluronidase-facilitated subcutaneous infusion of IgG in primary immunodeficiencies. Immunotherapy, 6(5), 553-567 (2014).

\* cited by examiner

SUBCUTANEOUS THERAPEUTIC ENZYME FORMULATIONS, USES, AND METHODS FOR GENERATING THEREOF

RELATED APPLICATIONS

This application claims benefit of priority to U.S. Ser. No. 62/145,424 filed Apr. 9, 2015, which is incorporated herein by reference in its entirety.

BACKGROUND OF THE INVENTION

Lysosomal storage diseases (LSDs) are a large group of disorders caused by the absence of functional enzymes used for the degradation of substances within lysosomes. Those affected by the disorder accumulate abnormal amounts of metabolic substrates in various organs causing morbidity and mortality.

SUMMARY OF THE INVENTION

Current treatments for lysosomal storage diseases rely on replacement of nonfunctional or absent enzymes. Such enzyme replacement therapies are only available as intravenous infusions, which require the establishment of a peripheral or central venous line into which the treatment fluid is delivered. These treatments are commonly administered in hospitals due to their complexity, demand of specialized equipment, and qualified medical personnel.

Described herein are compositions and methods for treating lysosomal storage diseases involving subcutaneous or transdermal delivery of replacement enzymes. Such methods and compositions avoid the problems and inconvenience associated with intravenous administration of replacement enzymes to treat LSDs. The compositions and methods disclosed herein provide pharmacological and patient-associated benefits stemming from subcutaneous or intradermal delivery, such as self-administration, pediatric or infant administration, multiple discrete dosing, reduction or elimination of infusion-related hypersensitivities and risk of infection, reduction of dose-dependent adverse reactions, relief of infusion related time expenditures, and extending the plasma half-life of the replacement enzyme.

Accordingly, in one aspect, there are provided compositions comprising, a lysosomal storage disorder replacement enzyme (LSDRE) and a dispersing agent, wherein the LSDRE and the dispersing agent are in a stable formulation. In some embodiments, the stable formulation is aqueous and is stable for at least 3 months when stored at 2-8° C. In some embodiments, the stable formulation is aqueous and is stable for at least 7 days when stored at 23-27° C. In some embodiments, the stable formulation is aqueous and is stable for at least 12 hours when stored at 35-37° C. In some embodiments, the stable formulation is lyophilized and is stable for at least 6 months when stored at 2-8° C. In some embodiments, the stable formulation is lyophilized and is stable for at least 7 days when stored at 23-27° C. after reconstitution. In some embodiments, the stable formulation is lyophilized and is stable for at least 12 hours when stored at 35-37° C. after reconstitution. In some embodiments, the LSDRE maintains at least 50% of its activity during storage. In some embodiments, the LSDRE maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In further or additional embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, or combinations thereof. In some embodiments in which the dispersing agent is an enzyme, the enzyme maintains at least 5% activity, at least 10% activity, at least 15% activity, at least 20% activity, at least 25% activity, at least 50% activity, at least 75% activity, at least 95% activity, including increments therein, during storage. In some embodiments, the dispersing agent enzyme maintains at least 5% activity, at least 10% activity, at least 15% activity, at least 20% activity, at least 25% activity, at least 50% activity, at least 75% activity, at least 95% activity, including increments therein, during storage. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the syringe comprises a first chamber and a second chamber, wherein the first chamber comprises a lyophilized form of the composition, and the second chamber comprises a pharmaceutically acceptable diluent for reconstitution of the composition. In some embodiments, the formulation is a multi-dose formulation. In some embodiments, the stable formulation comprises alpha-galactosidase A (GLA) and hyaluronidase. In some embodiments, the GLA is in an amount of about 1 mg/mL to about 5 mg/mL. In some embodiments, the hyaluronidase is in an amount suitable for facilitating subcutaneous or intradermal delivery of the LSDRE. In some embodiments, the GLA maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the hyaluronidase maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the stable formulation comprises alpha-galactosidase A (GLA) and hyaluronidase, wherein the stable formulation is at a pH of about 7. In some embodiments, the stable formulation comprises alpha-galactosidase A (GLA) and hyaluronidase, wherein the stable formulation is at a pH of about 7, and is stable at 2-8° C. for at least 12 weeks. In some embodiments, the stable formulation comprises alpha-galactosidase A (GLA) and hyaluronidase, wherein the stable formulation is at a pH of about 7, and is stable at 25° C. for at least 6 days. In some embodiments, the stable formulation comprises alpha-galactosidase A (GLA) and bovine hyaluronidase. In some embodiments, the stable formulation comprises about 1 to about 5 mg/mL alpha-galactosidase A (GLA) and about 50 to about 300 U/mL hyaluronidase. In some embodiments, the stable formulation comprises alpha-galactosidase A (GLA), hyaluronidase, buffer and polysorbate 20. In some embodiments, the composition is an aqueous solution. In some embodiments, the composition is lyophilized. In some embodiments, the composition is packaged in a pre-filled syringe. In further or additional embodiments, the syringe comprises a first chamber and a second chamber, wherein the first chamber comprises a lyophilized form of the composition, and the second chamber comprises a pharmaceutically acceptable diluent for reconstitution of the composition. In some embodiments, the formulation is a multi-dose formulation. In some embodiments, the stable formulation comprises alpha-galactosidase A (GLA) and hyaluronidase, wherein the stable formulation is aqueous. In some embodiments, the GLA maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the hyaluronidase maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the stable formulation comprises alpha-galactosidase A (GLA) and hyaluronidase, wherein the stable formulation is aqueous and is at a pH of about 7. In some embodiments, the stable formulation comprises alpha-galactosidase A (GLA) and hyaluronidase, wherein the stable formulation is aqueous, is at a pH of about 7, and is stable at 2-8° C. for at least 12 weeks. In some embodiments, the stable formulation comprises alpha-galactosidase A (GLA) and hyaluronidase, wherein the stable formulation is aqueous, is at a pH of about 7, and is stable at 25° C. for at least 6 days. In some embodiments, the stable formulation comprises alpha-galactosidase A (GLA) and bovine hyaluronidase, wherein the stable formulation is aqueous. In some embodiments, the stable formulation comprises about 1 to about 5 mg/mL alpha-galactosidase A (GLA) and about 50 to about 300 U/mL hyaluronidase, wherein the stable formulation is aqueous. In some embodiments, the stable formulation comprises alpha-galactosidase A (GLA), hyaluronidase, buffer, and polysorbate 20, wherein the stable formulation is aqueous. In some embodiments, the stable formulation comprises alpha-galactosidase A (GLA) and hyaluronidase, wherein the stable formulation is lyophilized. In some embodiments, the GLA maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the hyaluronidase maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the stable formulation comprises alpha-galactosidase A (GLA) and hyaluronidase, wherein the stable formulation is lyophilized and is at a pH of about 7. In some embodiments, the stable formulation comprises alpha-galactosidase A (GLA) and hyaluronidase, wherein the stable formulation is lyophilized, is at a pH of about 7, and is stable at 2-8° C. for at least 12 weeks. In some embodiments, the stable formulation comprises alpha-galactosidase A (GLA) and hyaluronidase, wherein the stable formulation is lyophilized, is at a pH of about 7, and is stable at 25° C. for at least 6 days. In some embodiments, the stable formulation comprises alpha-galactosidase A (GLA) and bovine hyaluronidase, wherein the stable formulation is lyophilized. In some embodiments, the stable formulation comprises about 1 to about 5 mg/mL alpha-galactosidase A (GLA) and about 50 to about 300 U/mL hyaluronidase, wherein the stable formulation is lyophilized. In some embodiments, the stable formulation comprises alpha-galactosidase A (GLA), hyaluronidase, buffer, and polysorbate 20, wherein the stable formulation is lyophilized.

In another aspect, there are provided compositions comprising, alpha-galactosidase A (GLA) and hyaluronidase, wherein the GLA and hyaluronidase are in a stable formulation. In some embodiments, the stable formulation is aqueous and is stable for at least 3 months when stored at 2-8° C. In some embodiments, the stable formulation is lyophilized and is stable for at least 6 months when stored at 2-8° C. In some embodiments, the GLA maintains at least 50% of its activity during storage. In some embodiments, the GLA is a mammalian GLA. In some embodiments, the GLA is recombinant. In some embodiments, the GLA is in an amount of about 1 mg/mL to about 5 mg/mL. In some embodiments, the hyaluronidase is in an amount suitable for facilitating subcutaneous or intradermal delivery of the GLA. In some embodiments, the hyaluronidase is in an amount corresponding to 1-1000 U, 100-1000 U, 250-1000 U, 1-5 U, 5-10 U, 10-50 U, 50-100 U, 100-200 U, 200-300 U, 300-500 U, or 500-1000 U per single unit dose. In some embodiments, the hyaluronidase is animal-derived. In some embodiments, the hyaluronidase is recombinant. In some embodiments, the composition is packaged in a pre-filled syringe. In some embodiments, syringe comprises a first chamber and a second chamber, wherein the first chamber comprises a lyophilized form of the composition, and the second chamber comprises a pharmaceutically acceptable diluent for reconstitution of the composition. In some embodiments, the composition is a multi-dose formulation.

In another aspect, there are provided compositions comprising a lysosomal storage disorder replacement enzyme (LSDRE) and a hyaluronidase, wherein the hyaluronidase is in an amount suitable for facilitating subcutaneous or intradermal delivery of the LSDRE. In some embodiments, the hyaluronidase is in an amount less than 1000 U per single unit dose. In some embodiments, the hyaluronidase is in an amount of about 150 U per single unit dose. In some embodiments, the hyaluronidase is in an amount of 50-300 U per single dose. In some embodiments, the hyaluronidase is in an amount corresponding to 1-1000 U, 100-1000 U, 250-1000 U, 1-5 U, 5-10 U, 10-50 U, 50-100 U, 100-200 U, 200-300 U, 300-500 U, or 500-1000 U per single unit dose. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, Acetyl-CoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the hyaluronidase is animal-derived. In some embodiments, the hyaluronidase is recombinant. In some embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the prefilled syringe comprises a first chamber and a second chamber, wherein the first chamber comprises a lyophilized form of the composition, and the second chamber comprises a pharmaceutically acceptable diluent for reconstitution of the composition. In some embodiments, the composition comprises alpha-galactosidase A (GLA) and hyaluronidase. In some embodiments, the composition comprises alpha-galactosidase A (GLA) and hyaluronidase, wherein the composition is at a pH of about 7. In some embodiments, the composition comprises alpha-galactosidase A (GLA) and hyaluronidase, wherein the composition is at a pH of about 7, and is stable at 2-8° C. for at least 12 weeks. In some embodiments, the composition comprises alpha-galactosidase A (GLA) and hyaluronidase, wherein the composition is at a pH of about 7, and is stable at 25° C. for at least 6 days. In some embodiments, the composition comprises alpha-galactosidase A (GLA) and bovine hyaluronidase. In some embodiments, the composition comprises about 1 to about 5 mg/mL alpha-galactosidase A (GLA) and about 50 to about 300 U/mL hyaluronidase. In some embodiments, the composition comprises alpha-galactosidase A (GLA), hyaluronidase, buffer and polysorbate 20.

In another aspect, there are provided compositions comprising an LSDRE and a dispersing agent, wherein the LSDRE is in a concentrated amount. In some embodiments, the LSDRE is in an amount of about 3 mg/mL or higher. In some embodiments, the LSDRE is in amount of 1 mg/ml or higher, 1.5 mg/ml or higher, 2 mg/ml or higher, 2.5 mg/ml or higher, 3 mg/ml or higher, 4 mg/ml or higher, 5 mg/ml or higher, 6 mg/ml or higher, 7 mg/ml or higher, 8 mg/ml or higher, 9 mg/ml or higher, 10 mg/ml or higher, 12 mg/ml or higher, 15 mg/ml or higher, 20 mg/ml or higher, 25 mg/ml or higher, 30 mg/ml or higher, 35 mg/ml or higher, 40 mg/ml or higher, 45 mg/ml or higher, or 50 mg/ml or higher, including increments therein. In some embodiments, the LSDRE is in an amount of about 1 mg/mL to about 5 mg/mL. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition. In some embodiments, the composition comprises about 1 to about 5 mg/mL alpha-galactosidase A (GLA) and about 50 to about 300 U/mL hyaluronidase.

In another aspect, there are provided compositions comprising an LSDRE and a hyaluronidase, wherein the LSDRE and hyaluronidase are in a ratio of 150,000,000 U LSDRE:1 U hyaluronidase to 3,000 U LSDRE:1 U hyaluronidase. In some embodiments, the LSDRE and hyaluronidase are in a ratio of 1,000,000 U LSDRE:1 U hyaluronidase to 10,000 U LSDRE:1 U hyaluronidase. In some embodiments, the LSDRE and hyaluronidase are in a ratio of 100,000 U LSDRE:1 U hyaluronidase to 5,000 U LSDRE:1 U hyaluronidase. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the composition comprises alpha-galactosidase A (GLA) and hyaluronidase. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the hyaluronidase is animal-derived. In some embodiments, the hyaluronidase is recombinant. In some embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided compositions comprising an LSDRE and a dispersing agent, wherein the dispersing agent facilitates subcutaneous or intradermal delivery of the LSDRE. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the composition comprises alpha-galactosidase A (GLA) and hyaluronidase. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided compositions comprising an LSDRE, a dispersing agent, and an excipient that facilitates subcutaneous or intradermal delivery. In some embodiments, the excipient is selected from the group consisting of a buffering agent, a non-ionic surfactant, a stabilizer, a preservative, and combinations thereof. In further or additional embodiments, the buffering agent is selected from the group consisting of phosphate, histidine, citrate and combinations thereof. In further or additional embodiments, the stabilizer is selected from the group consisting of mannitol, methionine, glycine, arginine, albumin, trehalose, sucrose and combinations thereof. In further or additional embodiments, the non-ionic surfactant is selected from the group consisting of polysorbate 20, polysorbate 80, poloxamer 188, polyethylene-polypropylene copolymer, and combinations thereof. In some embodiments, the preservative is meta-cresol, benzyl alcohol, or phenol. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the composition comprises alpha-galactosidase A (GLA), hyaluronidase, and an excipient that facilitates subcutaneous or intradermal delivery. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided compositions comprising an LSDRE and a dispersing agent, wherein the composition is formulated to give a $t_{max}$ of the LSDRE in a patient's bloodstream within 12 hours following administration of a single dose subcutaneous injection of the composition. In some embodiments, the $t_{max}$ of the LSDRE in a patient's bloodstream is reached following the administration of a single dose subcutaneous injection of the composition within 1 hour, 2 hours, 3 hours, 5 hours, 10 hours, 15 hours, 20 hours, or 24 hours, including increments therein. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is alpha-galactosidase A and the dispersing agent is hyaluronidase. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided compositions comprising an LSDRE and a dispersing agent, wherein the composition is formulated to give an AUC of the LSDRE in a patient's bloodstream following administration of a single dose subcutaneous injection of the composition of at least 25% of the AUC of the standard dose of the LSDRE administered by IV infusion. In some embodiments, the AUC of the LSDRE in a patient's bloodstream following administration of a single dose subcutaneous injection of the composition is at least 10%, 15%, 20%, 25%, 50%, 75%, 90%, or 95%, including increments therein, of the AUC of the standard dose. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is alpha-galactosidase A and the dispersing agent is hyaluronidase. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided compositions comprising an LSDRE and a dispersing agent, wherein the composition is formulated to give $C_{max}$ of the LSDRE in a patient's bloodstream following administration of a single dose subcutaneous injection of the composition of at least 25% of the $C_{max}$ of the standard dose of the LSDRE administered by IV infusion. In some embodiments, the $C_{max}$ of the LSDRE in a patient's bloodstream following administration of a single dose subcutaneous injection of the composition is at least 10%, 15%, 20%, 25%, 50%, 75%, 90%, or 95%, including increments therein, of the $C_{max}$ of the standard dose. In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is alpha-galactosidase A and the dispersing agent is hyaluronidase. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In some embodiments, the composition is aqueous and is stable for at least 3 months when stored at 2-8° C. In some embodiments, the composition is aqueous and is stable for at least 7 days when stored at 23-27° C. In some embodiments, the composition is aqueous and is stable for at least 12 hours when stored at 35-37° C. In some embodiments, the composition is lyophilized and is stable for at least 6 months when stored at 2-8° C. In some embodiments, the composition is lyophilized and is stable for at least 7 days when stored at 23-27° C. after reconstitution. In some embodiments, the composition is lyophilized and is stable for at least 12 hours when stored at 35-37° C. after reconstitution. In some embodiments, the LSDRE maintains at least 50% of its activity during storage. In some embodiments, the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, Acetyl-CoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof. In some embodiments, the LSDRE is alpha-galactosidase A. In some embodiments, the LSDRE is a mammalian LSDRE. In some embodiments, the LSDRE is a human LSDRE. In some embodiments, the LSDRE is recombinant. In some embodiments, the LSDRE is a modified form. In some embodiments, the dispersing agent is selected from the group consisting of hyaluronidase, collagenase, elastase, chondroitinase, and combinations thereof. In some embodiments, the dispersing agent is a hyaluronidase. In further or additional embodiments, the hyaluronidase is animal-derived. In further or additional embodiments, the hyaluronidase is recombinant. In further or additional embodiments, the hyaluronidase is a modified form. In some embodiments, the composition is an aqueous solution. In some embodiments, the composition is lyophilized. In some embodiments, the composition is packaged in a pre-filled syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition.

In another aspect, there are provided methods of treating a lysosomal storage disorder in a patient in need thereof comprising, administering subcutaneously or intradermally an effective amount of a composition described herein, wherein the composition comprises an LSDRE corresponding to the lysosomal storage disorder and a dispersant agent. In some embodiments, the lysosomal storage disorder is selected from the group consisting of Fabry disease, Gaucher disease, Pompe disease, Tay-Sachs disease, Sandhoff disease, Niemann-Pick disease, Krabbe disease, Farber disease, metachromatic leukodystrophy, MPS I (Hurler, Scheie, Hurler-Scheie), Hunter disease, MPS III (A, B, C, D), MPS IV (A, B), Maroteaux-Lamy disease, Sly disease, alpha mannosidosis, beta mannosidosis, fucosidosis, Schindler disease (I, II, III), Wolman, aspartylglucosaminuria, prosaposin deficiency, sulfatide activator deficiency, Gaucher activator deficiency. In further or additional embodiments, the lysosomal storage disorder is Fabry disease. In further or additional embodiments, Fabry disease is a form affecting multiple organs. In further or additional embodiments, Fabry disease is a form not exhibiting cerebrovascular complications. In some embodiments, the administering is by a subcutaneous injection. In some embodiments, the administering is subcutaneously or intradermally with a unit dose at a frequency selected from the group consisting of three times a day, twice a day, once a day, every other day, every three days, every four days, every five days, every six days, every week, and every two weeks. In further or additional embodiments, the unit dose is no more than 1.5 mL. In further or additional embodiments, the dispersant agent is hyaluronidase and is present at a concentration of 1-1000 U, 100-1000 U, 250-1000 U, 1-5 U, 5-10 U, 10-50 U, 50-100 U, 100-200 U, 200-300 U, 300-500 U, or 500-100 U per unit dose. In some embodiments, the LSDRE is alpha-galactosidase A and the dispersing agent is hyaluronidase. In some embodiments, the LSDRE is alpha-galactosidase and is present at a concentration of at least 3,000,000 U/mg USP, whereby the treatment dosage is between 0.05-3.0 mg/kg. In further or additional embodiments, the subcutaneous injection is administered to the patient's abdomen, thigh, or upper arm.

In another aspect, there are provided method of treating a lysosomal storage disorder in a patient in need thereof comprising, administering subcutaneously or intradermally a composition comprising an LSDRE corresponding to the lysosomal storage disorder and a dispersant agent. In some embodiments, the lysosomal storage disorder is selected from the group consisting of Fabry disease, Gaucher disease, Pompe disease, Tay-Sachs disease, Sandhoff disease, Niemann-Pick disease, Krabbe disease, Farber disease, metachromatic leukodystrophy, MPS I (Hurler, Scheie, Hurler-Scheie), Hunter disease, MPS III (A, B, C, D), MPS IV (A, B), Maroteaux-Lamy disease, Sly disease, alpha mannosidosis, beta mannosidosis, fucosidosis, Schindler disease (I, II, III), Wolman, aspartylglucosaminuria, prosaposin deficiency, sulfatide activator deficiency, Gaucher activator deficiency. In some embodiments, the lysosomal storage disorder is Fabry disease and the LSDRE is GLA. In some embodiments, the administering is subcutaneously or intradermally with a unit dose at a frequency selected from the group consisting of three times a day, twice a day, once a day, every other day, every three days, every four days, every five days, every six days, every week, and every two weeks. In some embodiments, the unit dose is no more than 1.5 mL. In some embodiments, the LSDRE is alpha-galactosidase and is present at a concentration of at least 3,000,000 U/mg USP, whereby the treatment dosage is between 0.05-3.0 mg/kg.

In another aspect, there is provided a kit comprising a pre-filled syringe comprising a unit dose of a composition of any of the formulations described herein and instructions for use. In some embodiments, the kits comprise a plurality of syringes each containing a unit dose of a composition described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawing of which:

DETAILED DESCRIPTION OF THE INVENTION

Figure 1:
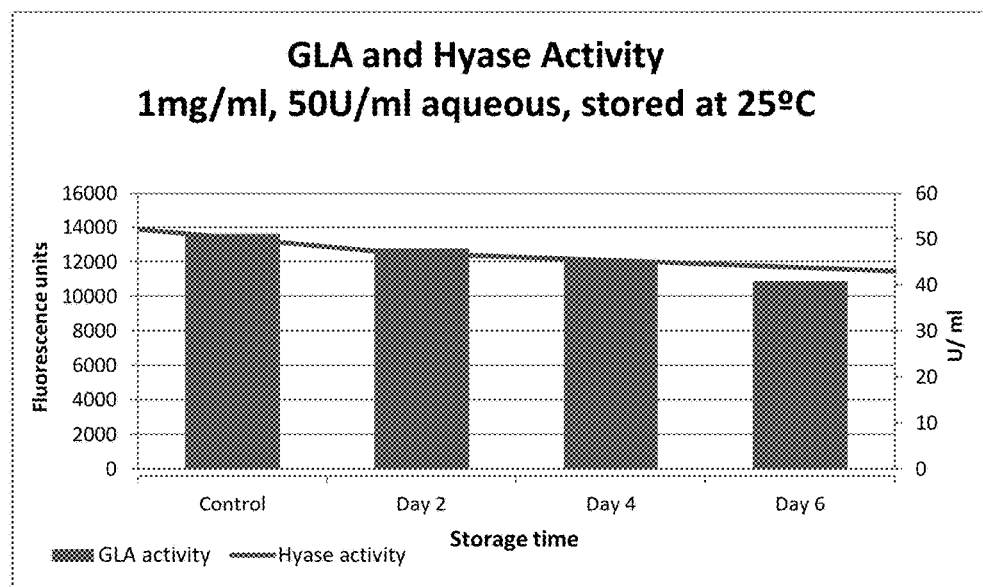
FIG. 1 illustrates alpha-galactosidase A (GLA) activity (bars) and hyaluronidase (Hyase) activity (lines) of Formulation A (GLA 1 mg/ml, Hyaluronidase 50 U/ml, 0.023% polysorbate 20, pH 7; Aqueous) on days 0 (control), 2, 4, and 6 during storage at 25° C.

Lysosomal storage diseases (LSDs) are a large group of disorders characterized by the absence of functional enzymes used for the degradation of substances within the lysosomes. Current treatments for lysosomal storage diseases involve complex intravenous enzyme replacement therapies. Intravenous therapies not only impose a significant economic burden, but also a therapeutic burden. Intravenous treatments possess multiple pharmacological drawbacks such as infusion related hypersensitivities to short plasma half-lives of the administered drug. Alternatives to intravenous treatments for lysosomal storage disorders are desired to improve patient compliance and treatment outcome in patients afflicted with these diseases. The formulations described herein, addresses the issues related to intravenous therapies by providing a lysosomal storage disease treatment that is suitable for subcutaneous or intradermal administration. In some embodiments, the formulation comprises of at least one lysosomal storage disorder replacement enzyme (LSDRE) and one dispersing agent to facilitate the subcutaneous tissue delivery of the LSDRE.

Fabry disease is an X-linked lysosomal storage disease that is characterized by the absence of functional alpha-galactosidase A (GLA) enzymes to metabolize glycosphingolipids in mammalian lysosomes. The absence of GLA ultimately leads to the accumulation of globotriaosylceramide (GL3) substrates in the kidney, heart, liver, and vascular endothelial tissues. The accumulation of GL3 affects the respective organs of these tissues causing morbidity. Prior to the introduction of recombinant alpha-galactosidase A (GLA) as an enzyme replacement therapy, treatment methods relied on symptomatic relief of progressive organ damage that clinically manifested as renal failure, cardiomyopathies, stroke, acroparesthesia, and angiokeratomas. Current GLA replacement therapies are only available as intravenous infusions. The intravenous treatment sessions for a patient with Fabry disease typically last several hours and must be repeated multiple times every month for life. The treatment not only imposes a significant economic burden, but also a therapeutic burden on the patients, thereby diminishing their quality of life.

Accordingly, described herein are compositions and methods for treating lysosomal storage diseases, such as Fabry disease, involving subcutaneous or transdermal delivery of replacement enzymes. Such methods and compositions avoid the problems and inconvenience associated with intravenous administration of replacement enzymes to treat LSDs.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20% or ±10%, or ±5%, or even ±1% from the specified value, as such variations are appropriate for the disclosed compositions or to perform the disclosed methods.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Stable Formulation

Disclosed herein, in some embodiments, are compositions comprising, a lysosomal storage disorder replacement enzyme (LSDRE) and a dispersing agent, wherein the LSDRE and the dispersing agent are in a stable formulation. In some embodiments a stable formulation contains a native or modified LSDRE and excipient(s) to compose a physiologically compatible aqueous-form or lyophilized-form mixture that is favorable for subcutaneous or intradermal administration. "Native" as used herein in reference to an enzyme refers to any wild-type enzyme having catalytic specificity toward its innate substrate. "Modified" as used herein in reference to an enzyme refers to any wild-type enzyme that has been mutated or altered to confer, enhance, or obviate catalytic activity towards its innate substrate and/or otherwise unrelated substrates.

In some embodiments, the composition comprises a lysosomal storage disorder replacement enzyme (LSDRE). Such LSDREs are used to treat patients having an LSD, which is characterized by a deficiency in an enzyme that degrades lipids or glycoproteins in lysosomes. LSDs are generally classified (ICD) into the following subgroups: lipid storage disorders, mucopolysaccharidoses, glycoprotein storage disorders, glycoprotein storage disorders and mucolipidoses. In some embodiments, the LSDRE is selected from the group consisting of alpha-galactosidase A, glucocerebrosidase, acid alpha-glucosidase, beta-hexosaminidase A, beta-hexosaminidase B, sphingomyelinase, galactocerebrosidase, acid ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, acid beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.

In some embodiments, the LSDRE is an alpha-galactosidase A (GLA), which belongs to the family of hydrolases. GLA catalyzes the hydrolysis of 0- and S-glycosyl compounds, specifically, the hydrolysis of terminal, non-reducing alpha-D-galactose residues in alpha-D-galactosides (galactose oligosaccharides, galactomannans, and galactolipids). Human GLA is a homodimer glycoprotein with multiple N-glycosylation sites per subunit (Asn 108, Asn 161, Asn 184). This enzyme hydrolyzes globortriaosylceramide (GL3) into galactose and lactosylceramide in lysosomes. The absence of adequate functional GLA leads to the accumulation of GL3 in the plasma and tissues, causing Fabry pathology. In further embodiments, the GLA is a mammalian GLA. In yet a further embodiment, the GLA is a human GLA. In some embodiments, the GLA is recombinant. In various embodiments, the GLA is a modified form. In some embodiments, the GLA comprises the sequence set forth in NCBI Accession No. NP_000160.1 (GI: 4504009). In some embodiments, the GLA is a functional fragment of the sequence set forth in NCBI Accession No. NP_000160.1 (GI: 4504009). The GLA enzyme can be obtained from tissue (e.g., human placenta) or produced using suitable genetically modified expression systems derived from human cells (e.g. HEK293, human fibroblasts, PERC.6, HeLa), other mammalian cells (e.g., CHO, BHK, COS), insect cells (e.g., *Drosophila melanogaster, Spodoptera frugiperda, Trichoplusia ni*), plant (e.g., carrot), and microbial cells (e.g., *E. coli, B. subtilis, L. lactis, S. cerevisiae, P. pastoris, K. lactis, Y. lipolytica*). In some embodiments, the minimum purity or specific activity of the GLA enzyme component to be used in the formulation is at least 3,000,000 U/mg USP.

In some embodiments, the LSDRE is glucocerebrosidase. In further embodiments, the glucocerebrosidase is a mammalian glucocerebrosidase. In yet a further embodiment, the glucocerebrosidase is a human glucocerebrosidase. In some embodiments, the glucocerebrosidase is recombinant. In various embodiments, the glucocerebrosidase is a modified form.

In some embodiments, the LSDRE is beta-hexomsaminidase. In further embodiments, the beta-hexomsaminidase is a mammalian beta-hexomsaminidase. In yet a further embodiment, the beta-hexomsaminidase is a human beta-hexomsaminidase. In some embodiments, the beta-hexomsaminidase is recombinant. In various embodiments, the beta-hexomsaminidase is a modified form.

In some embodiments, the composition comprises an LSDRE and an agent responsible for delivering the LSDRE throughout the body. This agent functions within the formulation to facilitate delivery of the LSDRE and improve the pharmacokinetic and pharmacodynamic profiles of the LSDRE.

In some embodiments, the composition comprises an LSDRE and a delivery adjuvant.

In some embodiments, the composition comprises an LSDRE and a delivery agent.

In some embodiments, the composition comprises an LSDRE and an absorption enhancer.

In some embodiments, the dispersing agent is selected from the group consisting of hyaluronidase, collagenase, elastase, chondroitinase, or combinations thereof. In some embodiments, the dispersing agent is a hyaluronidase. Hyaluronidases belong to a family of hydrolase enzymes that degrade glycosaminoglycans (GAG). Mammalian hyaluronidases catalyze hydrolysis of beta 1-4 linkages between N-acetyl-beta-D-glucosamine and D-glucoronate residues in hyaluronate, chondroitin, chondroitin 4- and 6-sulfates, and dermatan. These latter structures are absent in human recombinant glycoproteins. Hyaluronate or hyaluronan is a non-sulfated GAG and an important viscoelastic constituent of the interstitial matrix that forms part of the connective tissue, skin, cartilage and synovial fluid. This megadalton dissacharide composed of N-acetylglucosamine and glucoronic acid repeats is produced by fibroblasts and secreted into the hypodermal interstitium; its degradation occurs mainly in the lymph nodes, liver, and in-situ by way of lysosomal hyaluronidases and exoglycosidases. In humans, the subcutaneous tissue or hypodermis generates roughly half of the total hyaluronan in the body, out of which a third is turned over daily in the remodeling process. In some embodiments, the hyaluronidase is used as a localized and reversible drug dispersant to facilitate subcutaneous or intradermal delivery and improve the pharmacokinetic and clinical profiles of the LSDRE. Functionally, animal-derived hyaluronidases (e.g., bovine, bee) are catalytically active without N-glycan moieties, as opposed to recombinant human hyaluronidases; which require at least one N-glycosylation site as well as disulfide bonds for activity. In various embodiments, the hyaluronidase is recombinant. In some embodiments, the hyaluronidase is recombinant and is obtained from a mammalian, microbial, or plant expression systems. In some embodiments, the hyaluronidase is human. In some embodiments, the hyaluronidase comprises the sequence set forth in NCBI Accession No. NP_001167515.1 (GI: 291290979). In some embodiments, the hyaluronidase is a functional fragment of the sequence set forth in NCBI Accession No. NP_001167515.1 (GI: 291290979). In some embodiments, the hyaluronidase is a truncated form of the sequence set forth in NCBI Accession No. NP_001167515.1 (GI: 291290979). In some embodiments, the hyaluronidase is animal-derived. In some embodiments, the hyaluronidase is bovine. In some embodiments, the hyaluronidase comprises the sequence set forth in NCBI Accession No. AY297029.1 (GI:31616580). In some embodiments, the hyaluronidase is a functional fragment of the sequence set forth in NCBI Accession No. AY297029.1 (GI:31616580). In some embodiments, the animal-derived hyaluronidase is rHuPH20/Hylenex, Amphadase, Hyalase, Hydase, Hylase, Vitrase or Wydase. In yet a further embodiment, the hyaluronidase is a modified form. In some embodiments, the minimum purity or specific activity of the hyaluronidase component used in the formulation is at least 100,000 U/mg USP.

In some embodiments, the dispersing agent is a collagenase. In some embodiments, the dispersing agent is an elastase. In some embodiments, the dispersing agent is a chondroitinase.

In some embodiments, the LSDRE and dispersing agent are in stable formulation. A stable formulation means that the components do not adversely affect each other. In some embodiments, in which the dispersing agent is an enzyme, a stable formulation is formulated so that a dispersing agent enzyme and the LSDRE do not degrade each other. In some embodiments, in which the dispersing agent is an enzyme, a stable formulation is formulated so that the dispersing agent enzyme and the LSDRE do not substantially degrade each other. In some embodiments, in which the dispersing agent is an enzyme, a stable formulation is formulated so that the dispersing agent enzyme and the LSDRE do not reduce each other's enzymatic activity. In some embodiments, in which the dispersing agent is an enzyme, a stable formulation is formulated so that the dispersing agent enzyme and the LSDRE do not substantially reduce each other's enzymatic activity. The stability of a formulation can be conducted by methods known in the formulation art and include measuring over time the enzymatic activity of the LSDRE and dispersing agent in a formulation stored at a particular temperature. Enzymatic activity of an LSDRE or dispersing agent enzyme can be assayed by methods well-known in the art.

In some embodiments, the LSDRE and dispersing agent maintain clinically useful levels of enzymatic activity while in storage. Hyaluronidase enzyme activity can be detected by a modified turbidometric assay, where one unit is defined as a change of 0.330 absorbance units (600 nm) per minute at a pH of 5.7 at 37 C. The assays measure the consumption of substrate or production of product over time. In some embodiments, the LSDRE maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage. In some embodiments, the dispersing agent enzyme maintains at least 5% activity, at least 10% activity, at least 15% activity, at least 20% activity, at least 25% activity, at least 50% activity, at least 60% activity, at least 70% activity, at least 75% activity, at least 80% activity, at least 90% activity, at least 95% activity, including increments therein, during storage.

In some embodiments, the formulation is aqueous and is stable for at least 3 months, 4 months, 5 months, 6 months, or 1 year, including increments therein, when stored at 2-8° C. In various embodiments, the formulation is aqueous and is stable for at least 7 days, 8 days, 9 days, 10 days, or 15 days, including increments therein when stored at 23-27° C. In further embodiments, the formulation is aqueous and is stable for at least 12 hours, 13 hours, 14 hours, 15 hours, or 24 hours, including increments therein, when stored at 35-37° C. In some embodiments, the formulation is aqueous and is stable for at least 12 hours, 13 hours, 14 hours, 15 hours, or 24 hours, including increments therein, when stored at 35-37° C. In yet a further embodiment, the formulation is lyophilized and is stable for at least 6 months, 7 months, 8 months, 9 months, or 1 year, including increments therein, when stored at 2-8° C. In some embodiments, the formulation is lyophilized and is stable for at least 7 days, 8 days, 9 days, 10 days, or 15 days, including increments therein, after reconstitution when stored at 23-27° C. In some embodiments, the formulation is lyophilized and is stable for at least 12 hours, 13 hours, 14 hours, 15 hours, or 24 hours, including increments therein, after reconstitution when stored at 35-37° C.

In some embodiments, the stable formulation is an aqueous solution. In yet a further embodiment, the stable formulation is lyophilized. In some embodiments, the stable formulation is packaged in a pre-filled syringe.

Limiting Amount of Hyaluronidase

In some embodiments, the composition comprises a lysosomal storage disorder replacement enzyme (LSDRE) and a hyaluronidase, wherein the hyaluronidase is in an amount suitable for facilitating subcutaneous or intradermal delivery of the LSDRE. Hyaluronidases belong to a family of hydrolase enzymes that degrade glycosaminoglycans. Hyaluronidase is used to disperse co-administrated drugs. Limiting the amount of hyaluronidase serves to ensure that the LSDRE is delivered throughout the body, not including the brain or bone. In some embodiments, the hyaluronidase is in an amount less than 1000 U per single unit dose. In some embodiments, the hyaluronidase is in an amount of about 150 U per single unit dose. In some embodiments, the hyaluronidase is in an amount of 50-300 U per single dose. In yet a further embodiment, the hyaluronidase is in an amount corresponding to 1-1000 U, 100-1000 U, 250-1000 U, 1-5 U, 5-10 U, 10-50 U, 50-100 U, 100-200 U, 200-300 U, 300-500 U, or 500-1000 U per single unit dose, including increments therein. In various embodiments, the single unit dose is for a 5 kg, 10 kg, 20 kg, 30 kg, 50 kg, 75 kg, 100 kg, 150 kg, or 200 kg person, including increments therein.

Concentrated Formulation of Lysosomal Storage Disorder Replacement Enzyme

In some embodiments, there are provided highly concentrated therapeutic enzyme preparations comprising an LSDRE and a dispersing agent. In some embodiments, the composition comprises a concentrated LSDRE and a dispersing agent. In some embodiments, the LSDRE is in amount of 3 mg/ml or higher. In some embodiments, the LSDRE is in amount of 1 mg/ml or higher, 1.5 mg/ml or higher, 2 mg/ml or higher, 2.5 mg/ml or higher, 3 mg/ml or higher, 4 mg/ml or higher, 5 mg/ml or higher, 6 mg/ml or higher, 7 mg/ml or higher, 8 mg/ml or higher, 9 mg/ml or higher, 10 mg/ml or higher, 12 mg/ml or higher, 15 mg/ml or higher, 20 mg/ml or higher, 25 mg/ml or higher, 30 mg/ml or higher, 35 mg/ml or higher, 40 mg/ml or higher, 45 mg/ml or higher, or 50 mg/ml or higher, including increments therein. In some embodiments, the LSDRE is in amount of about 1 mg/ml to about 5 mg/ml.

Ratio of Lysosomal Storage Disorder Replacement Enzyme to Hyaluronidase

In some embodiments, the formulation comprises an LSDRE and hyaluronidase are in a ratio of 150,000,000 U LSDRE:1 U hyaluronidase to 3,000 U LSDRE:1 U hyaluronidase. In some embodiments, the LSDRE and hyaluronidase are in a ratio of 1,000,000 U LSDRE:1 U hyaluronidase to 10,000 U LSDRE:1 U hyaluronidase. In some embodiments, the LSDRE and hyaluronidase are in a ratio of 100,000 U LSDRE:1 U hyaluronidase to 5,000 U LSDRE:1 U hyaluronidase. In further embodiments, the LSDRE and hyaluronidase are in a ratio of 150 million U LSDRE:1 U hyaluronidase, 100 million U LSDRE:1 U hyaluronidase, 50 million U LSDRE:1 U hyaluronidase, 25 million U LSDRE:1 U hyaluronidase, 5 million U LSDRE:1 U hyaluronidase, 1 million:1, 500 thousand U LSDRE:1 U hyaluronidase, 100 thousand U LSDRE:1 U hyaluronidase, 50 thousand U LSDRE:1 U hyaluronidase, 15 thousand U LSDRE:1 U hyaluronidase, or 3 thousand U LSDRE:1 U hyaluronidase, 1 thousand U LSDRE:1 U hyaluronidase, including increments therein.

Subcutaneous or Intradermal Delivery

In some embodiments, the composition comprises an LSDRE and a dispersing agent, wherein the dispersing agent facilitates subcutaneous or intradermal delivery of the LSDRE. Current methods of treating lysosomal storage disorders involve lengthy intravenous infusion therapies. Subcutaneous or intradermal treatments offer patients a less complex and more convenient treatment that can also be self-administered. Subcutaneous tissue and the hypodermis generate roughly half of the total of hyaluronan in the body. Using a suitable dispersing agent with a LSDRE facilitates delivery of the formulation subcutaneously or intradermally.

Additional Excipients

In some embodiments, the composition comprises and LSDRE, a dispersing agent, and an excipient that facilitates subcutaneous or intradermal delivery. Excipients are often added for the purposes such as bulking up formulations or conferring therapeutic enhancement on the active ingredient. In some embodiments, the excipient(s) are selected from the group consisting of a buffering agent, a non-ionic surfactant, a stabilizer, a preservative, and combinations thereof. A buffering agent is used to maintain the pH of a solution near a chosen value. A non-ionic surfactant is a compound that lowers the surface tension between two liquids or a liquid and a solid. They may act as detergents, wetting agents, emulsifiers, foaming agents, or dispersants. Stabilizers are chemicals that tend to inhibit the reaction between two or more other chemicals. They are important in this context to prevent the degradation of the active ingredients such as the LSDRE and the dispersing agent. Preservatives are added to formulations in order to prevent decomposition of a composition from undesirable chemical changes.

In some embodiments, the buffering agent is selected from the group consisting of phosphate, histidine, citrate, and combinations thereof. In various embodiments, the buffering agent is histidine. In further embodiments, the buffering agent is citrate. In some embodiments, the embodiments, the non-ionic surfactant is selected from the group consisting of polysorbate 20, polysorbate 80, poloxamer 188, polyethylene-polypropylene copolymer, and combinations thereof. In various embodiments, the non-ionic surfactant is polysorbate 80. In further embodiments, the non-ionic surfactant is poloxamer 188. In some embodiments, the stabilizer is selected from the group consisting of mannitol, methionine, glycine, arginine, trehalose, sucrose, and combinations thereof. In yet a further embodiment, the stabilizer is mannitol. In various embodiments, the stabilizer is arginine.

In some embodiments, any suitable preservative or combination of preservatives is employed. The amounts of preservative components included in the present compositions are sufficient to be effective in preserving the compositions and can vary based on the specific preservative component employed, the specific composition involved, the specific application involved, and the like factors. In some embodiments, preservative concentrations are in the range of about 0.00001% to about 0.5% (w/v) of the composition. In some embodiments, other concentrations of certain preservatives are employed, as the skilled artisan can readily ascertain an effective amount of preservative for a given formulation.

Examples of suitable preservatives include, without limitation, benzalkonium chloride, methyl and ethyl parabens, hexetidine, phenyl mercuric salts and the like and mixtures thereof. Thus, in some embodiments, the preservatives include quaternary ammonium salts such as benzalkonium chloride and cetrimide, chlorobutanol, sorbic acid, boric acid, methyl and ethyl parabens, hexetidine, phenyl mercuric salts and any other preservatives known to be safe and effective when used in topical products, and mixtures thereof. In particular embodiments, the preservative is benzalkonium chloride. In some embodiments, the preservative is selected from the group consisting of meta-cresol, benzyl alcohol, phenol, and combinations thereof. In some embodiments, the preservative is meta-cresol. In various embodiments, the preservative is benzyl alcohol. In a further embodiment, the preservative is phenol.

In some embodiments, the composition is formulated to be at pH suitable for subcutaneous or intradermal injection. In some embodiments, the pH is between pH 5±1. In some embodiments, the pH is about 3 to about 7. In some embodiments, the pH is about 4 to about 6. In some embodiments, the pH is about 4.5 to about 5.5. In some embodiments, the pH is about 6.5 to about 7.5. In some embodiments, the pH is about 7. In some embodiments, the composition is formulated to an osmolality of 300±20 mOsm/kg.

In one embodiment, the pharmaceutical excipient is a buffering agent consisting of 1-10 mM phosphate, 1-10 mM histidine, 1-10 mM citrate, or a combination thereof to provide a pH of 5±2.

Pharmacokinetic (PK) Parameters

In some embodiments, the composition comprises an LSDRE and a dispersing agent, wherein the composition is formulated to give a $t_{max}$ of the LSDRE in a patient's bloodstream within 12 hours following administration of a single dose subcutaneous injection of the composition. The term "$t_{max}$" refers to the time required to reach the maximum serum or plasma concentration ($C_{max}$) of the LSDRE. In some embodiments, the $t_{max}$ of the LSDRE in a patient's bloodstream is reached following the administration of a single dose subcutaneous injection of the composition within 1 hour, 2 hours, 3 hours, 5 hours, 10 hours, 15 hours, 20 hours, or 24 hours, including increments therein.

"Blood plasma concentration" refers to the concentration of LSDRE in the plasma compartment of the blood of a subject. It is understood that the blood concentration of LSDRE may vary significantly between subjects, due to variability with respect to metabolism and/or possible interactions with other therapeutic agents. In accordance with one embodiment disclosed herein, the blood or plasma concentration of LSDRE may vary from subject to subject. Likewise, values such as maximum plasma concentration (Cmax) or time to reach maximum plasma concentration (Tmax), or total area under the plasma concentration time curve (AUC(0-00)) may vary from subject to subject. Due to this variability, the amount necessary to constitute "a therapeutically effective amount" of LSDRE may vary from subject to subject.

A "measurable serum concentration" or "measurable plasma concentration" describes the blood serum or blood plasma concentration, typically measured in mg, or ng of therapeutic agent per mL, dL, or L of blood serum, absorbed into the bloodstream after administration. As used herein, measurable plasma concentrations are typically measured in ng/ml or µg/ml or activity units/ml.

In some embodiments, the composition comprises an LSDRE and a dispersing agent, wherein the composition is formulated to give an AUC of the LSDRE in a patient's bloodstream following administration of a single dose subcutaneous injection of the composition of at least 25% of the AUC of the standard dose of the LSDRE administered by IV infusion. The term AUC or area under the curve is the definite integral of the plot of serum drug concentration versus time. The AUC represents the total exposure of the drug over time. In another embodiment, one unit dose administered subcutaneously is sufficient to achieve 50% ($AUC_{SQ}/AUC_{IV}$) bioavailability of an equivalent intravenous dose. In some embodiments, the standard dose of the LSDRE alpha galactosidase A is 0.2 mg/kg. In some embodiments, the AUC of the LSDRE in a patient's bloodstream following administration of a single dose subcutaneous injection of the composition is at least 10%, 15%, 20%, 25%, 50%, 75%, 90%, or 95%, including increments therein, of the AUC of the standard dose.

In some embodiments, the composition comprises an LSDRE and a dispersing agent, wherein the composition is formulated to give $C_{max}$ of the LSDRE in a patient's bloodstream following administration of a single dose subcutaneous injection of the composition of at least 25% of the $C_{max}$ of the standard dose of the LSDRE administered by IV infusion. The term $C_{max}$ pharmacokinetics refers to the maximum or peak serum concentration that a drug achieves in a specified compartment or test are of the body after the drug has been administered and prior to the administration of a secondary dose. In some embodiments, the standard dose of the LSDRE alpha galactosidase A is 0.2 mg/kg. In some embodiments, the $C_{max}$ of the LSDRE in a patient's bloodstream following administration of a single dose subcutaneous injection of the composition is at least 10%, 15%, 20%, 25%, 50%, 75%, 80%, 85%, 90%, or 95%, including increments therein, of the $C_{max}$ of the standard dose. In some embodiments, the hyaluronidase in the formulation is in sufficient quantity to achieve a systemic or serum LSDRE $C_{max}$ of at least 25-50%, 50-75%, and 75-100% as compared to an equivalent intravenous dose within 12 hours post-administration.

Methods of Treatment

In some embodiments, there are provided methods of treating a lysosomal storage disorder in a patient in need thereof comprising, administering subcutaneously or intradermally an effective amount of a composition described herein, wherein the composition comprises an LSDRE corresponding to the lysosomal storage disorder and a dispersant agent.

The terms "effective amount" or "therapeutically effective amount," as used herein, refer to a sufficient amount of an LSDRE being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including an LSDRE required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the LSDRE, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial. In some embodiments, and the treatment dosage is between 0.05-3.0 mg/kg or $0.15$-$9 \times 10^6$ U/kg.

The terms "subject," "patient," and "individual" are used interchangeably herein. As used herein, they refer to an animal. By way of example only, a subject may be, but is not limited to, a mammal including, but not limited to, a human. In some embodiment, the subject is a human. The terms do not require the supervision (whether continuous or intermittent) of a medical professional.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The terms "co-administration" or the like, as used herein, are meant to encompass administration of the selected therapeutic agents to a single patient, and are intended to include treatment regimens in which the agents are administered by the same or different route of administration or at the same or different time.

Subcutaneous refers to a treatment where the substance is administered to the layer of skin directly below the dermis and epidermis. In some embodiments, a lyophilized composition is reconstituted inside a sterile environment devoid of external intervention or user handling, such as in the compartments or chambers of an injectable syringe (e.g. EZMix, Lyo-ject, Lyogo, Lyo-DCPS). In this embodiment, the lyophilized composition is isolated from an aqueous carrier, vehicle, or diluent in separate compartments of a self-injected syringe system that the user can actuate to create the final injectable mixture. This separation allows for an easy-to-use injection system that maximizes product sterility, stability, and shelf-life. In some embodiments, a patient effects a subcutaneous administration by use of needle self-injectors (e.g., BD Physiojet), needle-free self-injectors (e.g., GentleJet, Injex, Bioject, Mini-ject, Intraject, LISA), injection pumps. In some embodiments, the subcutaneous administration volume of a single unit dose is no more than 1.5 mL. In further embodiments, the subcutaneous administration volume of a single unit dose is no more than 0.1 mL, 0.2 mL, 0.3 mL, 0.4 mL, 0.5 mL, 0.6 mL, 0.7 mL, 0.8 mL, 0.9 mL, 1.0 mL, 1.1 mL, 1.2 mL, 1.3 mL, 1.4 mL, 1.5 mL, 1.6 mL, 1.7 mL, 1.8 mL, 1.9 mL, 2.0 mL, or increments therein. In some embodiments, the subcutaneous injection is administered into the patient's abdomen. In a further embodiment, the subcutaneous injection is administered into the patient's thigh. In various embodiments, the subcutaneous injection is administered into the patient's upper arm.

Intradermal refers to a treatment administered into the dermis. Because the dermis is located directly underneath the upper skin layer a shorter needle, such as a micro needle can easily reach it. Using a micro needle provides benefits such as evoking less pain in the patient and preventing needle-stick injuries. Administering intradermal treatments can also be accomplished through needle free self-injectors and injection pumps. Additionally, since the amount of drug administered is small, utilizing intradermal injections can save on amount of drug used and therefore cut down on cost of the treatment.

In some embodiments, the treatment of a lysosomal storage disorder comprises administering a composition disclosed herein to a patient having Fabry disease. In some embodiments, the composition comprises GLA and hyaluronidase. In further embodiments, the treatment of a lysosomal storage disease comprises administering a composition disclosed herein to a patient having Gaucher disease. In some embodiments, the subcutaneous or intradermal treatment is administered at a unit dose frequency of three times a day, twice, a day, once a day, twice a week, once a week, twice a month, or once a month, including increments therein.

Dosage Forms

Disclosed herein, in some embodiments, are dosage forms comprising an LSDRE and a dispersing agent suitable for subcutaneous or intradermal injection and including a physiologically acceptable sterile aqueous or non-aqueous solutions, dispersions, suspensions or emulsions, and sterile powders for reconstitution into sterile injectable solutions or dispersions. In some embodiments, the dosage form is an aqueous solution. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some embodiments, it is also desirable to include isotonic agents, such as sugars, sodium chloride, and the like.

In some embodiments, the aqueous solutions comprising the LSDRE and dispersing agent are lyophilized into a powder. Methods of lyophilization are well known in the art. Also provided are methods of reconstituting a lyophilized powder by adding a sterile aqueous diluent to the powder to form a reconstituted aqueous solution.

Kits

For use in the therapeutic methods of use described herein, kits and articles of manufacture are also described herein. In some embodiments, the kits include a package or container that is compartmentalized to receive one or more containers such as syringes, vials, and the like, each of the compartment(s) comprising one of the separate elements to be used in a method described herein. In some embodiments, the kit comprises a syringe comprising a unit dose of a composition of any of the formulations described herein and instructions for use. In some embodiments, the composition is an aqueous solution pre-filled into a syringe. In further or additional embodiments, the pre-filled syringe comprises a first chamber and a second chamber, wherein the first chamber comprises a lyophilized form of the composition, and the second chamber comprises a pharmaceutically acceptable diluent for reconstitution of the composition. In some embodiments, the kit comprises a plurality of single dose syringes. In some embodiments, the kit comprises a multi-dose vial and a plurality of syringes.

The term "acceptable" or "pharmaceutically acceptable", with respect to a formulation, composition or ingredient, as used herein, means having no persistent detrimental effect on the general health of the subject being treated or does not abrogate the biological activity or properties of the composition, and is relatively nontoxic.

The term "diluent" refers to chemical compounds that are used to dilute the composition of interest prior to delivery. Diluents can also be used to stabilize the composition because they can provide a more stable environment. Salts dissolved in buffered solutions (which also can provide pH control or maintenance) are utilized as diluents in the art, including, but not limited to a phosphate buffered saline solution.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Illustrative Embodiments

Provided below are illustrative embodiments of the invention:
1. A composition comprising, a lysosomal storage disorder replacement enzyme (LSDRE) and a dispersing agent, wherein the LSDRE and the dispersing agent are in a stable formulation.
2. The composition of embodiment 1, wherein the stable formulation is aqueous and is stable for at least 3 months when stored at 2-8° C.
3. The composition embodiment 1, wherein the stable formulation is aqueous and is stable for at least 7 days when stored at 23-27° C.
4. The composition of embodiment 1, wherein the stable formulation is aqueous and is stable for at least 12 hours when stored at 35-37° C.
5. The composition of embodiment 1, wherein the stable formulation is lyophilized and is stable for at least 6 months when stored at 2-8° C.
6. The composition of embodiment 1, wherein the stable formulation is lyophilized and is stable for at least 7 days when stored at 23-27° C. after reconstitution.
7. The composition of embodiment 1, wherein the stable formulation is lyophilized and is stable for at least 12 hours when stored at 35-37° C. after reconstitution.
8. The composition of any one of embodiments 1-7, wherein the LSDRE maintains at least 50% of its activity during storage.
9. The composition of any one of embodiments 1-8, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
10. The composition of any of embodiments 1-9, wherein the LSDRE is alpha-galactosidase A.
11. The composition of any of embodiments 1-10, wherein the LSDRE is a mammalian LSDRE.
12. The composition of any of embodiments 1-11, wherein the LSDRE is a human LSDRE.
13. The composition of any of embodiments 1-12, wherein the LSDRE is recombinant.
14. The composition of any of embodiments 1-13, wherein the LSDRE is a modified form.
15. The composition of any of embodiments 1-14, wherein the dispersing agent is selected from the group consisting of hyaluronidase, collagenase, elastase, chondroitinase, or combinations thereof.
16. The composition of any of embodiments 1-15, wherein the dispersing agent is a hyaluronidase.
17. The composition of embodiment 16, wherein the hyaluronidase is animal-derived.
18. The composition of embodiment 16, wherein the hyaluronidase is recombinant.
19. The composition of embodiment 16, wherein the hyaluronidase is a modified form.
20. The composition of any of embodiments 1-19, wherein the composition is an aqueous solution.
21. The composition of any of embodiments 1-19, wherein the composition is lyophilized.
22. The composition of any of embodiments 1-21, wherein the composition is packaged in a pre-filled syringe.
23. The composition of embodiment 22, wherein syringe comprises a first chamber and a second chamber, wherein the first chamber comprises a lyophilized form of the composition, and the second chamber comprises a pharmaceutically acceptable diluent for reconstitution of the composition.
24. A composition comprising a lysosomal storage disorder replacement enzyme (LSDRE) and a hyaluronidase, wherein the hyaluronidase is in an amount suitable for facilitating subcutaneous or intradermal delivery of the LSDRE.
25. The composition of embodiment 24, wherein the hyaluronidase is in an amount less than 1000 U per single unit dose.
26. The composition of embodiment 24, wherein the hyaluronidase is in an amount corresponding to 1-1000 U, 100-1000 U, 250-1000 U, 1-5 U, 5-10 U, 10-50 U, 50-100 U, 100-200 U, 200-300 U, 300-500 U, or 500-1000 U per single unit dose.

27. The composition of embodiment 24, wherein the composition is aqueous and is stable for at least 3 months when stored at 2-8° C.
28. The composition embodiment 24, wherein the composition is aqueous and is stable for at least 7 days when stored at 23-27° C.
29. The composition of embodiment 24, wherein the composition is aqueous and is stable for at least 12 hours when stored at 35-37° C.
30. The composition of embodiment 24, wherein the composition is lyophilized and is stable for at least 6 months when stored at 2-8° C.
31. The composition of embodiment 24, wherein the composition is lyophilized and is stable for at least 7 days when stored at 23-27° C. after reconstitution.
32. The composition of embodiment 24, wherein the composition is lyophilized and is stable for at least 12 hours when stored at 35-37° C. after reconstitution.
33. The composition of any of embodiments 24-32, wherein the LSDRE maintains at least 50% of its activity during storage.
34. The composition of any of embodiments 24-33, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
35. The composition of any of embodiments 24-34, wherein the LSDRE is alpha-galactosidase A.
36. The composition of any of embodiments 24-35, wherein the LSDRE is a mammalian LSDRE.
37. The composition of any of embodiments 24-36, wherein the LSDRE is a human LSDRE.
38. The composition of any of embodiments 24-37, wherein the LSDRE is recombinant.
39. The composition of any of embodiments 24-38, wherein the LSDRE is a modified form.
40. The composition of any of embodiments 24-39, wherein the hyaluronidase is animal-derived.
41. The composition of any of embodiments 24-39, wherein the hyaluronidase is recombinant.
42. The composition of any of embodiments 24-41, wherein the hyaluronidase is a modified form.
43. The composition of any of embodiments 24-42, wherein the composition is an aqueous solution.
44. The composition of any of embodiments 24-42, wherein the composition is lyophilized.
45. The composition of any of embodiments 24-44, wherein the composition is packaged in a pre-filled syringe.
46. The composition of embodiment 45, wherein the prefilled syringe comprises a first chamber and a second chamber, wherein the first chamber comprises a lyophilized form of the composition, and the second chamber comprises a pharmaceutically acceptable diluent for reconstitution of the composition.
47. A composition comprising an LSDRE and a dispersing agent, wherein the LSDRE is in an amount of about 3 mg/mL or higher.
48. The composition of embodiment 47, wherein the composition is aqueous and is stable for at least 3 months when stored at 2-8° C.
49. The composition embodiment 47, wherein the composition is aqueous and is stable for at least 7 days when stored at 23-27° C.
50. The composition of embodiment 47, wherein the composition is aqueous and is stable for at least 12 hours when stored at 35-37° C.
51. The composition of embodiment 47, wherein the composition is lyophilized and is stable for at least 6 months when stored at 2-8° C.
52. The composition of embodiment 47, wherein the composition is lyophilized and is stable for at least 7 days when stored at 23-27° C. after reconstitution.
53. The composition of embodiment 47, wherein the composition is lyophilized and is stable for at least 12 hours when stored at 35-37° C. after reconstitution.
54. The composition of any of embodiments 47-53, wherein the LSDRE maintains at least 50% of its activity during storage.
55. The composition of any of embodiments 47-54, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
56. The composition of any of embodiments 47-55, wherein the LSDRE is alpha-galactosidase A.
57. The composition of any of embodiments 47-56, wherein the LSDRE is a mammalian LSDRE.
58. The composition of any of embodiments 47-57, wherein the LSDRE is a human LSDRE.
59. The composition of any of embodiments 47-58, wherein the LSDRE is recombinant.
60. The composition of any of embodiments 47-59, wherein the LSDRE is a modified form.
61. The composition of any of embodiments 47-60, wherein the dispersing agent is selected from the group consisting of hyaluronidase, collagenase, elastase, chondroitinase, and combinations thereof.
62. The composition of any of embodiments 47-61, wherein the dispersing agent is a hyaluronidase.
63. The composition of embodiment 62, wherein the hyaluronidase is animal-derived.
64. The composition of embodiment 62, wherein the hyaluronidase is recombinant.
65. The composition of embodiment 62, wherein the hyaluronidase is a modified form.
66. The composition of any of embodiments 47-65, wherein the composition is an aqueous solution.
67. The composition of any of embodiments 47-65, wherein the composition is lyophilized.

68. The composition of any of embodiments 47-67, wherein the composition is packaged in a pre-filled syringe.
69. The composition of embodiment 68, wherein the pre-filled syringe comprises a first chamber and a second chamber, wherein the first chamber comprises a lyophilized form of the composition, and the second chamber comprises a pharmaceutically acceptable diluent for reconstitution of the composition.
70. A composition comprising an LSDRE and a hyaluronidase, wherein the LSDRE and hyaluronidase are in a ratio of 150 million:1 to 3 thousand:1—expressed as enzyme activity units LSDRE/activity units of HAase.
71. The composition of embodiment 70, wherein the composition is aqueous and is stable for at least 3 months when stored at 2-8° C.
72. The composition embodiment 70, wherein the composition is aqueous and is stable for at least 7 days when stored at 23-27° C.
73. The composition of embodiment 70, wherein the composition is aqueous and is stable for at least 12 hours when stored at 35-37° C.
74. The composition of embodiment 70, wherein the composition is lyophilized and is stable for at least 6 months when stored at 2-8° C.
75. The composition of embodiment 70, wherein the composition is lyophilized and is stable for at least 7 days when stored at 23-27° C. after reconstitution.
76. The composition of embodiment 70, wherein the composition is lyophilized and is stable for at least 12 hours when stored at 35-37° C. after reconstitution.
77. The composition of any of embodiments 70-76, wherein the LSDRE maintains at least 50% of its activity during storage.
78. The composition of any of embodiments 70-77, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
79. The composition of any of embodiments 70-78, wherein the LSDRE is alpha-galactosidase A.
80. The composition of any of embodiments 70-79, wherein the LSDRE is a mammalian LSDRE.
81. The composition of any of embodiments 70-80, wherein the LSDRE is a human LSDRE.
82. The composition of any of embodiments 70-81, wherein the LSDRE is recombinant.
83. The composition of any of embodiments 70-82, wherein the LSDRE is a modified form.
84. The composition of any of embodiments 70-83, wherein the hyaluronidase is animal-derived.
85. The composition of any of embodiments 70-83, wherein the hyaluronidase is recombinant.
86. The composition of any of embodiments 70-85, wherein the hyaluronidase is a modified form.
87. The composition of any of embodiments 70-86, wherein the composition is an aqueous solution.
88. The composition of any of embodiments 70-86, wherein the composition is lyophilized.
89. The composition of any of embodiments 70-88, wherein the composition is packaged in a pre-filled syringe.
90. The composition of embodiment 89, wherein the pre-filled syringe comprises a first chamber and a second chamber, wherein the first chamber comprises a lyophilized form of the composition, and the second chamber comprises a pharmaceutically acceptable diluent for reconstitution of the composition.
91. A composition comprising, an LSDRE and a dispersing agent, wherein the dispersing agent facilitates subcutaneous or intradermal delivery of the LSDRE.
92. The composition of embodiment 91, wherein the composition is aqueous and is stable for at least 3 months when stored at 2-8° C.
93. The composition embodiment 91, wherein the composition is aqueous and is stable for at least 7 days when stored at 23-27° C.
94. The composition of embodiment 91, wherein the composition is aqueous and is stable for at least 12 hours when stored at 35-37° C.
95. The composition of embodiment 91, wherein the composition is lyophilized and is stable for at least 6 months when stored at 2-8° C.
96. The composition of embodiment 91, wherein the composition is lyophilized and is stable for at least 7 days when stored at 23-27° C. after reconstitution.
97. The composition of embodiment 91, wherein the composition is lyophilized and is stable for at least 12 hours when stored at 35-37° C. after reconstitution.
98. The composition of any of embodiments 91-97, wherein the LSDRE maintains at least 50% of its activity during storage.
99. The composition of any of embodiments 91-98, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
100. The composition of any of embodiments 91-99, wherein the LSDRE is alpha-galactosidase A.
101. The composition of any of embodiments 91-100, wherein the LSDRE is a mammalian LSDRE.
102. The composition of any of embodiments 91-101, wherein the LSDRE is a human LSDRE.
103. The composition of any of embodiments 91-102, wherein the LSDRE is recombinant.
104. The composition of any of embodiments 91-103, wherein the LSDRE is a modified form.
105. The composition of any of embodiments 91-104, wherein the dispersing agent is selected from the group consisting of hyaluronidase, collagenase, elastase, chondroitinase, and combinations thereof.

106. The composition of any of embodiments 91-105, wherein the dispersing agent is a hyaluronidase.
107. The composition of embodiment 106, wherein the hyaluronidase is animal-derived.
108. The composition of embodiment 106, wherein the hyaluronidase is recombinant.
109. The composition of embodiment 106, wherein the hyaluronidase is a modified form.
110. The composition of any of embodiments 91-109, wherein the composition is an aqueous solution.
111. The composition of any of embodiments 91-109, wherein the composition is lyophilized.
112. The composition of any of embodiments 91-111, wherein the composition is packaged in a pre-filled syringe.
113. The composition of embodiment 112, wherein the pre-filled syringe comprises a first chamber and a second chamber, wherein the first chamber comprises a lyophilized form of the composition, and the second chamber comprises a pharmaceutically acceptable diluent for reconstitution of the composition.
114. A composition comprising an LSDRE, a dispersing agent, and an excipient that facilitates subcutaneous or intradermal delivery.
115. The composition of embodiment 114, wherein the excipient is selected from the group consisting of a buffering agent, a non-ionic surfactant, a stabilizer, a preservative, and combinations thereof.
116. The composition of embodiment 115, wherein the buffering agent is selected from the group consisting of phosphate, histidine, citrate and combinations thereof.
117. The composition of embodiment 115, wherein the stabilizer is selected from the group consisting of mannitol, methionine, glycine, arginine, albumin, trehalose, sucrose and combinations thereof.
118. The composition of embodiment 115, wherein the non-ionic surfactant is selected from the group consisting of polysorbate 20, polysorbate 80, poloxamer 188, polyethylene-polypropylene copolymer, and combinations thereof.
119. The composition of any of embodiments 114-118, wherein the composition is aqueous and is stable for at least 3 months when stored at 2-8° C.
120. The composition of any of embodiments 114-118, wherein the composition is aqueous and is stable for at least 7 days when stored at 23-27° C.
121. The composition of any of embodiments 114-118, wherein the composition is aqueous and is stable for at least 12 hours when stored at 35-37° C.
122. The composition of any of embodiments 114-118, wherein the composition is lyophilized and is stable for at least 6 months when stored at 2-8° C.
123. The composition of any of embodiments 114-118, wherein the composition is lyophilized and is stable for at least 7 days when stored at 23-27° C. after reconstitution.
124. The composition of any of embodiments 114-118, wherein the composition is lyophilized and is stable for at least 12 hours when stored at 35-37° C. after reconstitution.
125. The composition of any of embodiments 114-124, wherein the LSDRE maintains at least 50% of its activity during storage.
126. The composition of any of embodiments 114-125, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.
127. The composition of any of embodiments 114-126, wherein the LSDRE is alpha-galactosidase A.
128. The composition of any of embodiments 114-127, wherein the LSDRE is a mammalian LSDRE.
129. The composition of any of embodiments 114-128, wherein the LSDRE is a human LSDRE.
130. The composition of any of embodiments 114-129, wherein the LSDRE is recombinant.
131. The composition of any of embodiments 114-130, wherein the LSDRE is a modified form.
132. The composition of any of embodiments 114-131, wherein the dispersing agent is selected from the group consisting of hyaluronidase, collagenase, elastase, chondroitinase, and combinations thereof.
133. The composition of any of embodiments 114-132, wherein the dispersing agent is a hyaluronidase.
134. The composition of embodiment 133, wherein the hyaluronidase is animal-derived.
135. The composition of embodiment 133, wherein the hyaluronidase is recombinant.
136. The composition of embodiment 133, wherein the hyaluronidase is a modified form.
137. The composition of any of embodiments 114-136, wherein the composition is an aqueous solution.
138. The composition of any of embodiments 114-136, wherein the composition is lyophilized.
139. The composition of any of embodiments 114-138, wherein the composition is packaged in a pre-filled syringe.
140. The composition of embodiment 139, wherein the pre-filled syringe comprises a first chamber and a second chamber, wherein the first chamber comprises a lyophilized form of the composition, and the second chamber comprises a pharmaceutically acceptable diluent for reconstitution of the composition.
141. A composition comprising, an LSDRE and a dispersing agent, wherein the composition is formulated to give a $t_{max}$ of the LSDRE in a patient's bloodstream within 12 hours following administration of a single dose subcutaneous injection of the composition.
142. A composition comprising, an LSDRE and a dispersing agent, wherein the composition is formulated to give an AUC of the LSDRE in a patient's bloodstream following administration of a single dose subcutaneous injection of the composition of at least 25% of the AUC of the standard dose of the LSDRE administered by IV infusion.
143. A composition comprising, an LSDRE and a dispersing agent, wherein the composition is formulated to give $C_{max}$ of the LSDRE in a patient's bloodstream following administration of a single dose subcutaneous injection of the composition of at least 25% of the $C_{max}$ of the standard dose of the LSDRE administered by IV infusion.

144. The composition of any of embodiments 141-143, wherein the composition is aqueous and is stable for at least 3 months when stored at 2-8° C.

145. The composition of any of embodiments 141-143, wherein the composition is aqueous and is stable for at least 7 days when stored at 23-27° C.

146. The composition of any of embodiments 141-143, wherein the composition is aqueous and is stable for at least 12 hours when stored at 35-37° C.

147. The composition of any of embodiments 141-143, wherein the composition is lyophilized and is stable for at least 6 months when stored at 2-8° C.

148. The composition of any of embodiments 141-143, wherein the composition is lyophilized and is stable for at least 7 days when stored at 23-27° C. after reconstitution.

149. The composition of any of embodiments 141-143, wherein the composition is lyophilized and is stable for at least 12 hours when stored at 35-37° C. after reconstitution.

150. The composition of any of embodiments 141-149, wherein the LSDRE maintains at least 50% of its activity during storage.

151. The composition of any one of embodiments 141-150, wherein the LSDRE is selected from the group consisting of alpha-galactosidase A, glucocerebrosidase, alpha-glucosidase, beta-hexosaminidase A, beta-hexosaminidase B, sphingomyelinase, galactocerebrosidase, ceramidase, arylsulfatase A, alpha-L-iduronidase, iduronate-2-sulfatase, heparan-S-sulfate sulfamidase, N-acetyl-D-glucosaminidase, AcetylCoA-glucosaminide N-acetyltransferase, N-acetyl-glucosaminine-6-sulfate, N-Acetylgalactosamine-6-sulfate sulfatase, beta-galactosidase, arylsulfatase B, beta-glucuronidase, alpha-mannosidase, beta-mannosidase, alpha-L-fucosidase, sialidase, N-acetylgalactosaminidase, lysosomal acid lipase, N-aspartylglucosaminidase, prosaposin, saposins (A, B, C, D), and combinations thereof.

152. The composition of any one of embodiments 141-151, wherein the LSDRE is alpha-galactosidase A.

153. The composition of any one of embodiments 141-152, wherein the LSDRE is a mammalian LSDRE.

154. The composition of any one of embodiments 141-153, wherein the LSDRE is a human LSDRE.

155. The composition of any one of embodiments 141-154, wherein the LSDRE is recombinant.

156. The composition of any one of embodiments 141-155, wherein the LSDRE is a modified form.

157. The composition of any one of embodiments 141-156, wherein the dispersing agent is selected from the group consisting of hyaluronidase, collagenase, elastase, chondroitinase, and combinations thereof.

158. The composition of embodiment 141-157, wherein the dispersing agent is a hyaluronidase.

159. The composition of embodiment 158, wherein the hyaluronidase is animal-derived.

160. The composition of embodiment 158, wherein the hyaluronidase is recombinant.

161. The composition of embodiment 158, wherein the hyaluronidase is a modified form.

162. The composition of any one of embodiments 141-161, wherein the composition is an aqueous solution.

163. The composition of any one of embodiments 141-161, wherein the composition is lyophilized.

164. The composition of any one of embodiments 141-163, wherein the composition is packaged in a pre-filled syringe.

165. The composition of embodiment 164, wherein the pre-filled syringe comprises a first chamber and a second chamber, wherein the first chamber comprises a lyophilized form of the composition, and the second chamber comprises a pharmaceutically acceptable diluent for reconstitution of the composition.

166. A method of treating a lysosomal storage disorder in a patient in need thereof comprising, administering subcutaneously or intradermally a composition of any of embodiments 1-165, wherein the composition comprises an LSDRE corresponding to the lysosomal storage disorder and a dispersant agent.

167. The method of embodiment 166, wherein the lysosomal storage disorder is selected from the group consisting of Fabry disease, Gaucher disease, Pompe disease, Tay-Sachs disease, Sandhoff disease, Niemann-Pick disease, Krabbe disease, Farber disease, metachromatic leukodystrophy, MPS I (Hurler, Scheie, Hurler-Scheie), Hunter disease, MPS III (A, B, C, D), MPS IV (A, B), Maroteaux-Lamy disease, Sly disease, alpha mannosidosis, beta mannosidosis, fucosidosis, Schindler disease (I, II, III), Wolman, aspartylglucosaminuria, prosaposin deficiency, sulfatide activator deficiency, Gaucher activator deficiency.

168. The method of embodiment 167, wherein the lysosomal storage disorder is Fabry disease.

169. The method of embodiment 168, wherein the Fabry disease is a form affecting multiple organs.

170. The method of embodiment 168, wherein the Fabry disease is a form not exhibiting cerebrovascular complications.

171. The method of embodiment 166, wherein the administering is by a subcutaneous injection.

172. The method of embodiment 166, wherein the administering is subcutaneously or intradermally with a unit dose at a frequency selected from the group consisting of three times a day, twice a day, once a day, every other day, every three days, every four days, every five days, every six days, every week, and every two weeks.

173. The method of embodiment 172, wherein the unit dose is no more than 1.5 mL.

174. The method of embodiment 172, wherein the dispersant agent is hyaluronidase and is present at a concentration of 1-1000 U, 100-1000 U, 250-1000 U, 1-5 U, 5-10 U, 10-50 U, 50-100 U, 100-200 U, 200-300 U, 300-500 U, or 500-100 U per unit dose.

175. The method of embodiment 166, wherein the LSDRE is alpha-galactosidase and is present at a concentration of at least 3,000,000 U/mg USP, whereby the treatment dosage is between 0.05-3.0 mg/kg.

176. The method of embodiment 171, wherein the subcutaneous injection is administered to the patient's abdomen, thigh, or upper arm.

177. A kit comprising a syringe comprising a unit dose of a composition of any of embodiments 1-165 and instructions for use.

EXAMPLES

Example 1: Potency—GLA

Artificial GLA enzyme (EC3.2.1.22) substrates 4MU-Gal (4MU-alpha-D-galactopyranoside) and pNP-Gal (p-nitrophenyl-alpha-D-galactopyranoside) is used to determine the stability of the aqueous and lyophilized preparations (pH 3-7±0.5) stored at temperatures 2-8° C., 23-27° C., and 35-37° C. and incubation times (0-3±1 months), (0-7±1 days), (0-12±1 hours) respectively. The enzyme activity at time 0 is standardized to be 100% as baseline. The 4MU-Gal reaction is carried out at a substrate concentration of 10 mM and quenched after 15 min with NaOH. The fluorescence is read at (excitation 365 nm, emission 460 nm) against a 4MU standard curve. The pNP-Gal reaction is carried out at a substrate concentration of 33 mM and quenched after 10 min with NaOH with absorbance determined at 405 nm.

The viability of stable formulations is also examined in vitro by the cleavage of GL3 accumulated in cultured Fabry patient fibroblasts with untreated Fabry fibroblasts as controls. GLA samples from each stable formulation are added to the culture medium to an activity level of 5 umol/h/ml and cells are cultured for 72 hrs at 37° C. Immunostaining is performed on accumulated GL3 with anti-GLA mouse antibody.

Example 2: Potency—Hyaluronidase

The enzyme activity of mammalian hyaluronidases (EC3.2.1.35) can be detected by a modified (Sigma-Aldrich) turbidometric assay based on the USP XXIII-NF XVIII standards, whereby one unit is defined as a change of 0.330 absorbance units (600 nm) per minute at pH 5.7 at 37° C. Samples are drawn from the stable aqueous and lyophilized preparations (pH 3-7±0.5) stored at temperatures 2-8° C., 23-27° C., and 35-37° C. and incubation times (0-3±1 months), (0-7±1 days), (0-12±1 hours) respectively.

Example 3: N-Glycosylation

N-glycan stability for GLA and hyaluronidase is assayed by isoelectric focusing (IEF), whereby the banding pattern of the different formulations is assessed and compared to the baseline. Samples from the stable aqueous and lyophilized preparations (pH 3-7±0.5) stored at temperatures 2-8° C., 23-27° C., and 35-37° C. and incubation times (0-3±1 months), (0-7±1 days), (0-12±1 hours) respectively are drawn and loaded on a pH 3-7 IEF gel run with premade buffer. Focusing is done for 1 hour (at 100V), 1 hour (at 200V), and 30 minutes (at 500V). Gels are stained with PhastGel Coomassie Blue R-350 and then destained in methanol/acetic acid for 2 hours. Additionally, IEF banding patterns is complemented and correlated with ion exchange chromatography (IEX) to determine elution profiles and charge stability on major glycoforms present at baseline and at different storage time points.

Example 4: Purity

Purity and molecular mass is determined by SDS-PAGE gel electrophoresis followed by Coomassie brilliant blue R staining on samples from the stable aqueous and lyophilized preparations (pH 3-7±0.5) stored at temperatures 2-8° C., 23-27° C., and 35-37° C. and incubation times (0-3±1 months), (0-7±1 days), (0-12±1 hours) respectively. Banding patterns of baseline conditions are used as standards (monomer weight 51 kDa).

Example 5: SEC

Purity of all stable samples is determined by size exclusion chromatography (SEC) to yield monomer, high molecular weight, and low molecular weight compositions. Elution profiles of baseline conditions are used as standards.

Example 6: Pharmacokinetics

Jugular-vein cannulated Sprague-Dawley rats are used to characterize subcutaneous versus intravenous administration of radioactive iodinated GLA at three doses: 0.1 mg/kg, 1 mg/kg, and 5 mg/kg. Intravenous administration and blood sampling is performed via a venous catheter at predetermined time points. Radiation is sampled through an automated gamma counter to determine $C_{max}$, $t_{max}$, and AUC.

Example 7: Exemplary Formulations

Formulation A:
Formulation A is an example of a stable aqueous formulation comprising an LSDRE, hyaluronidase, buffering agent, stabilizer, and a non-ionic surfactant.
Ingredients
Alpha galactosidase 5 mg/ml
Hyaluronidase 300 U/ml (bovine/ovine)
10 mM L-histidine
100 mM trehalose dihydrate
0.02% poloxamer 188
pH 5.5
Formulation B:
Formulation B is an example of a stable aqueous formulation comprising an LSDRE, hyaluronidase, buffering agent, and a non-ionic surfactant.
Ingredients
alpha galactosidase 5 mg/ml
hyaluronidase 300 U/ml (human)
10 mM PBS
0.02% polysorbate 80
pH 6.5
Formulation C:
Formulation C is an example of a stable lyophilized formulation comprising an LSDRE, hyaluronidase, buffering agent, stabilizer, and a non-ionic surfactant.
Ingredients
Alpha galactosidase 5 mg
Hyaluronidase 300 U (human)
30 mg mannitol
3 g sodium phosphate monobasic monohydrate
9 g sodium phosphate dibasic heptahydrate
Reconstituted to 5 mg/ml and 150 U/ml
pH 6.5

Example 8: Stability Studies

Samples of formulations A, B, and C are stored at 2-8° C., 23-27° C., or 35-37° C. and various assays are conducted at set time points to determine the stability of the formulations. Samples stored at 2-8° C. are assayed at the following time points: days 0, 7, 14, 21, 28, 35, 42, 49, 56, 63, 70, 84, and 91. Samples stored at 23-27° C. are assayed at the following time points: days 0, 1, 2, 3, 4, 5, 6, and 7. Samples stored at 35-37 C are assayed at the following time points: hours 0, 1, 2, 3, 4, 5, 6, 7, 8, 9, 10, 11, and 12. At each time point the following measurements are conducted: Alpha galactosidase A activity is measured as described in Example 1. Hyaluronidase activity is measured as described in Example 2. Monomer, high molecular weight, and low molecular weight compositions are measured through size exclusion chromatography as described in example 5. N-glycan stability for GLA and hyaluronidase is measured by isoelectric focusing (IEF) as described in example 3. Purity and molecular mass are measured by SDS-PAGE gel electrophoresis as described in example 4.

Example 9: Subcutaneous Injection of a Lyophilized Formulation

This example describes treating a patient with Fabry disease with subcutaneous injections of a composition provided herein. A lyophilized dose of a formulation of GLA and hyaluronidase having an amount sufficient to achieve a systemic or serum alpha-galactosidase A $t_{max}$ within 12 hours post-administration of a single dose is reconstituted in approximately 1.5 mL of a pharmaceutically-acceptable sterile vehicle. The reconstituted GLA/hyaluronidase solution is injected subcutaneously into the patient's upper arm at a weekly dosing frequency. The dosing frequency is adjusted to maximize the reduction in the patient's symptoms.

Example 10: Clinical Trial

Objectives of the study are (1) to examine the safety and efficacy of a subcutaneously administered formulation comprising alpha galactosidase A and recombinant human hyaluronidase in patients with Fabry Disease; (2) to characterize the pharmacokinetics and pharmacodynamics of the subcutaneously administered formulation; and (3) to assess the immunogenicity of the formulation following subcutaneous administration.

Primary outcome measures will comprise of incidence and severity of adverse events, number of subjects with local injection site reactions, and number of subjects that discontinue or withdraw from the study. Secondary outcome measures will comprise measuring alpha galactosidase A levels and hyaluronidase levels throughout the body.

Two treatment groups include (1) A standard dose of alpha galactosidase A of 0.2 mg/kg with 500 U of recombinant human hyaluronidase is administered twice weekly for four weeks; and (2) a standard dose of alpha galactosidase A of 0.2 mg/kg with 1000 U of recombinant human hyaluronidase is administered twice weekly for four weeks. The treatments are subcutaneously administered into the subject's upper arm.

Blood samples are collected on days 0, 1, 3, 5, 7, 14, 21, 28, and 35 to determine pharmacokinetic profiles.

Eligible subject must have received a diagnosis of Fabry disease. Additionally, subjects must not have received any treatments nor have an allergy to hyaluronidase.

Example 11: Stability Studies

Stability studies were conducted on Formulation A and Formulation B in aqueous form and Formulations C and D in lyophilized form and stored at 4° C. or 25° C.

Figure 2:
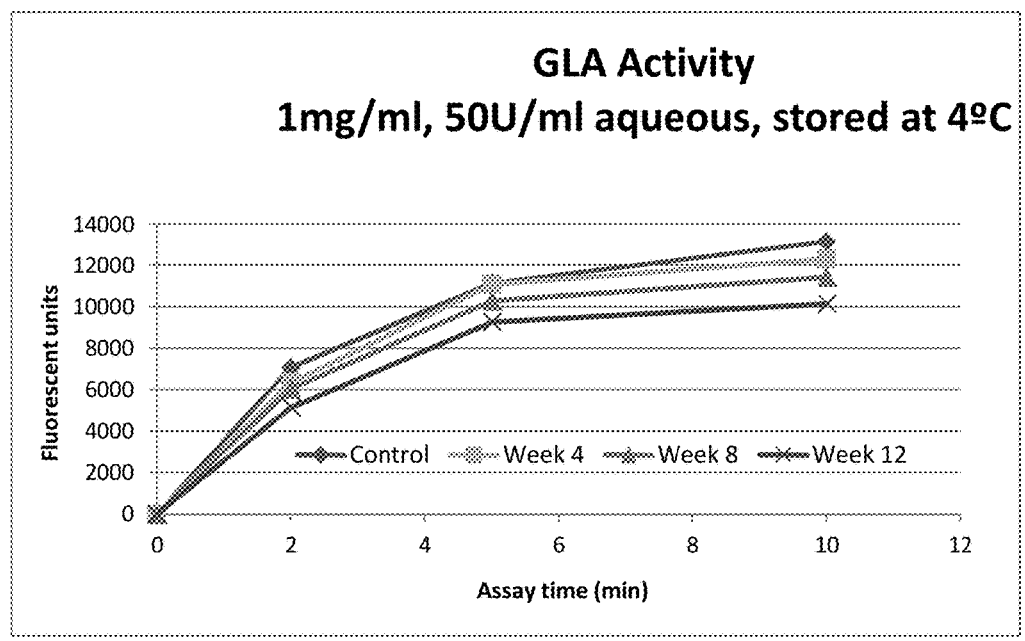
FIG. 2 illustrates GLA activity of Formulation A (GLA 1 mg/ml, Hyaluronidase 50 U/ml, 0.023% polysorbate 20, pH 7; Aqueous) on weeks 0 (control), 4, 8, and 12 during storage at 4° C., following 0, 2, 4, 6, 8, or 10 minutes of fluorometric assay time.

Formulation A was an aqueous preparation of alpha galactosidase A (GLA) (Sino Biological, Beijing, China) with specific activity of 3.36×10⁶ U/mg and bovine hyaluronidase (Sigma-Aldrich St. Louis, Mo.) in sodium phosphate buffer at concentrations of 1 mg/ml and 50 U/ml, respectively. Polysorbate 20 at 0.23 mg/ml was added to the solution and pH was adjusted to pH 7 with sodium hydroxide. Aliquots of 300 μl were stored in 1.0 ml borosilicate glass vials (Wheaton, Millville, N.J.) at 4° C. for 12 weeks or at 25° C. for 6 days. Baseline control at 4° C. was assessed after overnight incubation and control for 25° C. was determined immediately after formulation. All samples were diluted prior to the activity assays. The stability and individual enzyme potency for GLA and hyaluronidase were determined according to the method below and data are provided in Tables 1-3 and FIGS. 1-2). GLA activity was determined via a fluorometric assay by the conversion of 4-methylumbelliferyl α-D-galactopyranoside (4MUG) substrate to 4-methylumbelliferone (4MU), whereby one unit is defined as the amount of enzyme required to convert 1 nmole of 4MUG to 4MU in one hour at 37° C. Samples were read at 10 minutes assay incubation time (Tables 1, 2, 4, 5, 7, 8, 10 and 11) or the indicated assay time (Tables 3, 6, 9, and 12) using Nanodrop fluorometer (Thermo Scientific, Wilmington, Del.) at excitation and emission wavelengths of 365 and 450 nm respectively. HYAL activity was determined via a turbidimetric assay whereby one unit of activity will cause a change in A600 of 0.330 per minute at pH 5.35 at 37° C. in a 2.0 ml reaction mixture (45 minute assay). Each reaction consisted of 0.335-0.75 ml of enzyme solution incubated with 1 ml of hyaluronic acid. The resulting turbidity was read using a Clariostar spectrophotometer (BMG Labtech, Ortenberg, Germany) with % transmittance determined at 600 nm.

TABLE 1

GLA and Hyase activity of Formulation A (GLA 1 mg/ml, Hyaluronidase 50 U/ml, 0.023% polysorbate 20, pH 7; Aqueous) on weeks 0 (control), 4, 8, and 12 during storage at 4° C.

| Temperature | Storage time | GLA activity (FU t = 10) | % GLA activity | Hyase activity (U/ml) | % Hyase activity |
| --- | --- | --- | --- | --- | --- |
| 4 C. | Control (overnight storage) | 13156 | 100% | 47 | 100% |
| | Week 4 | 12307 | 94% | 38 | 81% |
| | Week 8 | 11424 | 87% | 44 | 94% |
| | Week 12 | 10138 | 77% | 49 | 104% |

TABLE 2

GLA and Hyase activity of Formulation A (GLA 1 mg/ml, Hyaluronidase 50 U/ml, 0.023% polysorbate 20, pH 7; Aqueous) on days 0 (control), 2, 4, and 6 during storage at 25° C.

| | | GLA activity | % GLA activity | Hyase activity | % Hyase activity |
| --- | --- | --- | --- | --- | --- |
| 25 C. | Control (immediately after formulation) | 13624 | 100% | 52 | 100% |
| | Day 2 | 12761 | 94% | 47 | 90% |
| | Day 4 | 12096 | 89% | 45 | 87% |
| | Day 6 | 10908 | 80% | 43 | 83% |

TABLE 3

GLA activity of Formulation A (GLA 1 mg/ml, Hyaluronidase 50 U/ml, 0.023% polysorbate 20, pH 7; Aqueous) on weeks 0 (control), 4, 8, and 12 during storage at 4° C., following 0, 2, 5, or 10 minutes of fluorometric assay time.

| GLA Activity 4 C. Time (min) | Control | Week 4 | Week 8 | Week 12 |
| --- | --- | --- | --- | --- |
| 0 | 0 | 0 | 0 | 0 |
| 2 | 7076 | 6337 | 6044 | 5141 |

TABLE 3-continued

GLA activity of Formulation A (GLA 1 mg/ml,
Hyaluronidase 50 U/ml, 0.023% polysorbate 20,
pH 7; Aqueous) on weeks 0 (control), 4, 8, and
12 during storage at 4° C., following 0, 2, 5,
or 10 minutes of fluorometric assay time.

| GLA Activity 4 C. Time (min) | Control | Week 4 | Week 8 | Week 12 |
|---|---|---|---|---|
| 5 | 11133 | 11085 | 10273 | 9258 |
| 10 | 13156 | 12307 | 11424 | 10138 |

Figure 3:
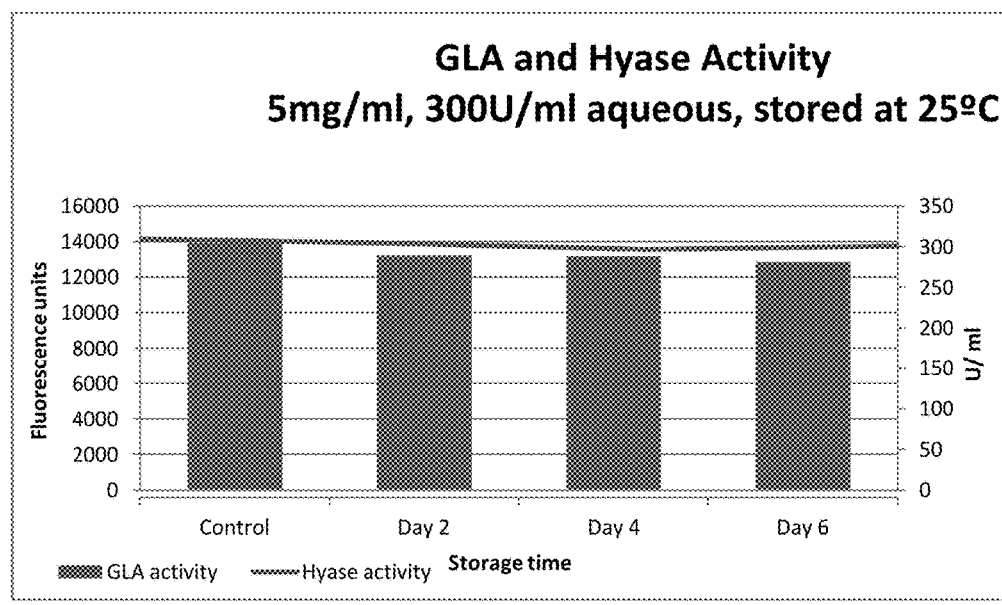
FIG. 3 illustrates GLA activity (bars) and Hyase activity (lines) of Formulation B (GLA 5 mg/ml, Hyaluronidase 300 U/ml, 0.023% polysorbate 20, pH 7; Aqueous) on days 0 (control), 2, 4, and 6 during storage at 25° C.
Figure 4:
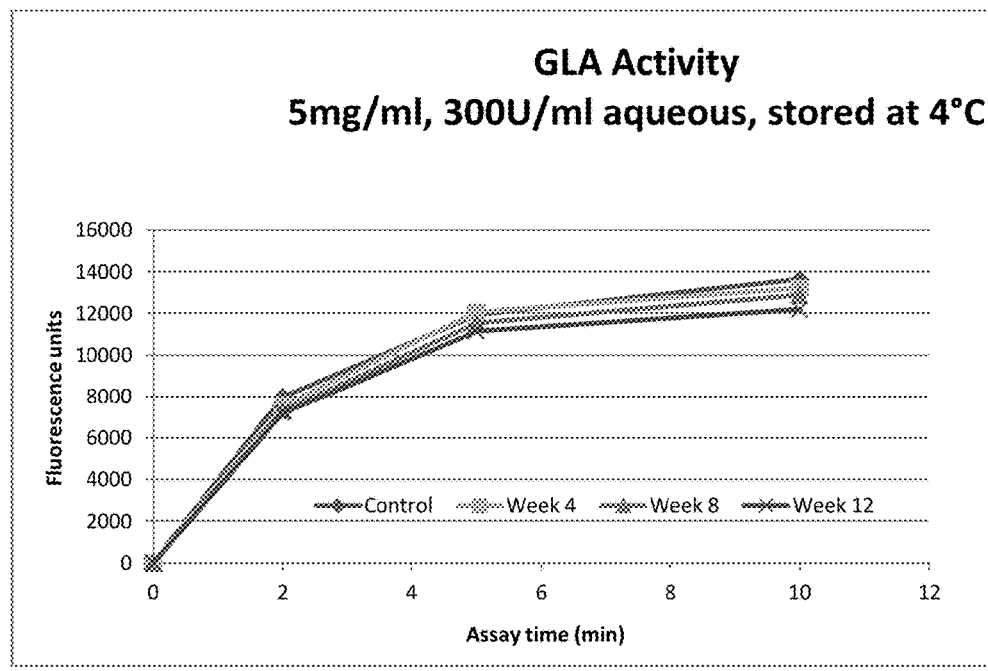
FIG. 4 illustrates GLA activity of Formulation B (GLA 5 mg/ml, Hyaluronidase 300 U/ml, 0.023% polysorbate 20, pH 7; Aqueous) on weeks 0 (control), 4, 8, and 12 during storage at 4° C., following 0, 2, 4, 6, 8, or 10 minutes of fluorometric assay time.

Formulation B was an aqueous preparation of GLA and bovine hyaluronidase in sodium phosphate buffer at concentrations of 5 mg/ml and 300 U/ml, respectively. Polysorbate 20 at 0.23 mg/ml was added to the solution and pH was adjusted to pH 7 with sodium hydroxide. Aliquots of 300 µl were stored in 1.0 ml borosilicate glass vials at 4° C. for 12 weeks or at 25° C. for 6 days. The stability and individual enzyme potency were determined (Tables 4-6, and FIGS. 3-4).

TABLE 4

GLA and Hyase activity of Formulation B (GLA 5 mg/ml,
Hyaluronidase 300 U/ml, 0.023% polysorbate 20, pH 7; Aqueous)
on weeks 0 (control), 4, 8, and 12 during storage at 4° C.

| Temperature | Storage time | GLA activity (FU t = 10) | % GLA activity | Hyase activity (U/ml) | % Hyase activity |
|---|---|---|---|---|---|
| 4 C. | Control (overnight storage) | 13635 | 100% | 319 | 100% |
|  | Week 4 | 13209 | 97% | 314 | 98% |
|  | Week 8 | 12882 | 94% | 302 | 95% |
|  | Week 12 | 12194 | 89% | 308 | 97% |

TABLE 5

GLA and Hyase activity of Formulation B (GLA 5 mg/ml,
Hyaluronidase 300 U/ml, 0.023% polysorbate 20, pH 7; Aqueous)
on days 0 (control), 2, 4, and 6 during storage at 25° C.

|  |  | GLA activity | % GLA activity | Hyase activity | % Hyase activity |
|---|---|---|---|---|---|
| 25 C. | Control (immediately after formulation) | 13941 | 100% | 310 | 100% |
|  | Day 2 | 13263 | 95% | 304 | 98% |
|  | Day 4 | 13204 | 95% | 297 | 96% |
|  | Day 6 | 12878 | 92% | 301 | 97% |

TABLE 6

GLA activity of Formulation B (GLA 5 mg/ml, Hyaluronidase
300 U/ml, 0.023% polysorbate 20, pH 7; Aqueous) on weeks
0 (control), 4, 8, and 12 during storage at 4° C., following
0, 2, 5, or 10 minutes of fluorometric assay time.

| Time (min) | Control | Week 4 | Week 8 | Week 12 |
|---|---|---|---|---|
| 0 | 0 | 0 | 0 | 0 |
| 2 | 7986 | 7580 | 7342 | 7211 |
| 5 | 11922 | 12053 | 11532 | 11146 |
| 10 | 13635 | 13209 | 12882 | 12194 |

Figure 5:
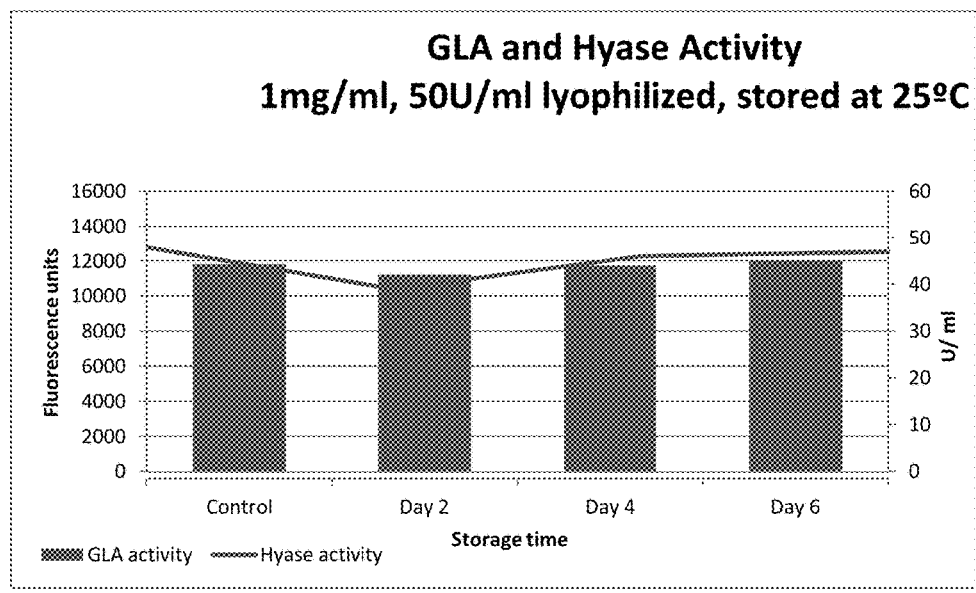
FIG. 5 illustrates GLA activity (bars) and Hyase activity (lines) of Formulation C (GLA 1 mg/ml, Hyaluronidase 50 U/ml, 6 mg/ml mannitol, sodium phosphate, pH 7; Lyophilized) on days 0 (control), 2, 4, and 6 during storage at 25° C.
Figure 6:
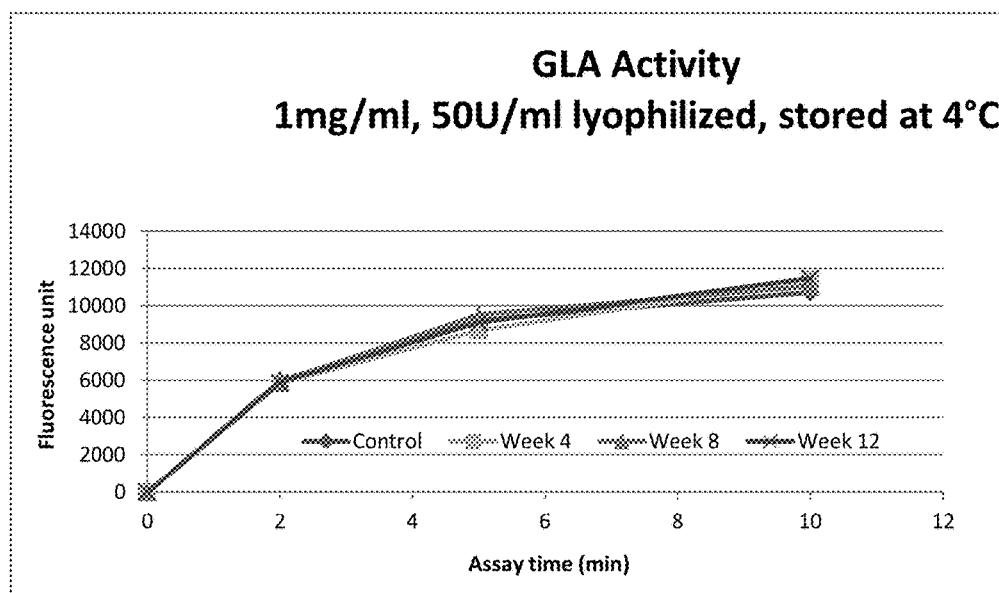
FIG. 6 illustrates GLA activity of Formulation C (GLA 1 mg/ml, Hyaluronidase 50 U/ml, 6 mg/ml mannitol, sodium phosphate, pH 7; Lyophilized) on weeks 0 (control), 4, 8, and 12 during storage at 4° C., following 0, 2, 4, 6, 8, or 10 minutes of fluorometric assay time.

Formulation C (GLA 1 mg/ml, Hyaluronidase 50 U/ml, 6 mg/ml mannitol, sodium phosphate, pH 7; Lyophilized) was a lyophilized preparation of GLA and bovine hyaluronidase in sodium phosphate buffer at concentrations of 1 mg/ml and 50 U/ml respectively. Polysorbate 20 at 0.23 mg/ml was added to the solution and adjusted to pH 7 with sodium hydroxide. Aliquots of 300 µl are lyophilized in Freezone Triad chamber system (Labconco, Kansas City, Mo.) and stored in 1.0 ml borosilicate glass vials at 4° C. for 12 weeks and at 25° C. for 6 days. Baseline control at 4° C. was assessed after overnight incubation and control for 25° C. was assayed immediately after formulation and lyophilization. All samples were reconstituted with purified water (EMD Millipore, Darmstadt, Germany) and diluted prior to assays. The stability and individual enzyme potency were determined according to the tables 7-9, and is illustrated in FIGS. 5-6.

TABLE 7

GLA and Hyase activity of Formulation C (GLA 1 mg/ml,
Hyaluronidase 50 U/ml, 6 mg/ml mannitol, sodium
phosphate, pH 7; Lyophilized) on weeks 0 (control),
4, 8, and 12 during storage at 4° C.

| Temperature | Storage time | GLA activity (FU t = 10) | % GLA activity | Hyase activity (U/ml) | % Hyase activity |
|---|---|---|---|---|---|
| 4 C. | Control (overnight storage) | 10704 | 100% | 51 | 100% |
|  | Week 4 | 11365 | 106% | 49 | 96% |
|  | Week 8 | 11034 | 103% | 41 | 80% |
|  | Week 12 | 11483 | 107% | 46 | 90% |

TABLE 8

GLA and Hyase activity of Formulation C (GLA 1 mg/ml,
Hyaluronidase 50 U/ml, 6 mg/ml mannitol, sodium phosphate, pH 7;
Lyophilized) on days 0 (control), 2, 4, and 6 during storage at 25° C.

|  |  | GLA activity | % GLA activity | Hyase activity | % Hyase activity |
|---|---|---|---|---|---|
| 25 C. | Control (immediately after formulation/ lyophilization) | 11838 | 100% | 48 | 100% |
|  | Day 2 | 11219 | 95% | 39 | 81% |
|  | Day 4 | 11750 | 99% | 46 | 96% |
|  | Day 6 | 12007 | 101% | 47 | 98% |

TABLE 9

GLA activity of Formulation C (GLA 1 mg/ml,
Hyaluronidase 50 U/ml, 6 mg/ml mannitol, sodium
phosphate, pH 7; Lyophilized) on weeks 0 (control),
4, 8, and 12 during storage at 4° C., following
0, 2, 5, or 10 minutes of fluorometric assay time.

| Time (min) | Control | Week 4 | Week 8 | Week 12 |
|---|---|---|---|---|
| 0 | 0 | 0 | 0 | 0 |
| 2 | 6002 | 5834 | 5915 | 5884 |
| 5 | 9210 | 8671 | 9501 | 9086 |
| 10 | 10704 | 11365 | 11034 | 11483 |

Figure 7:
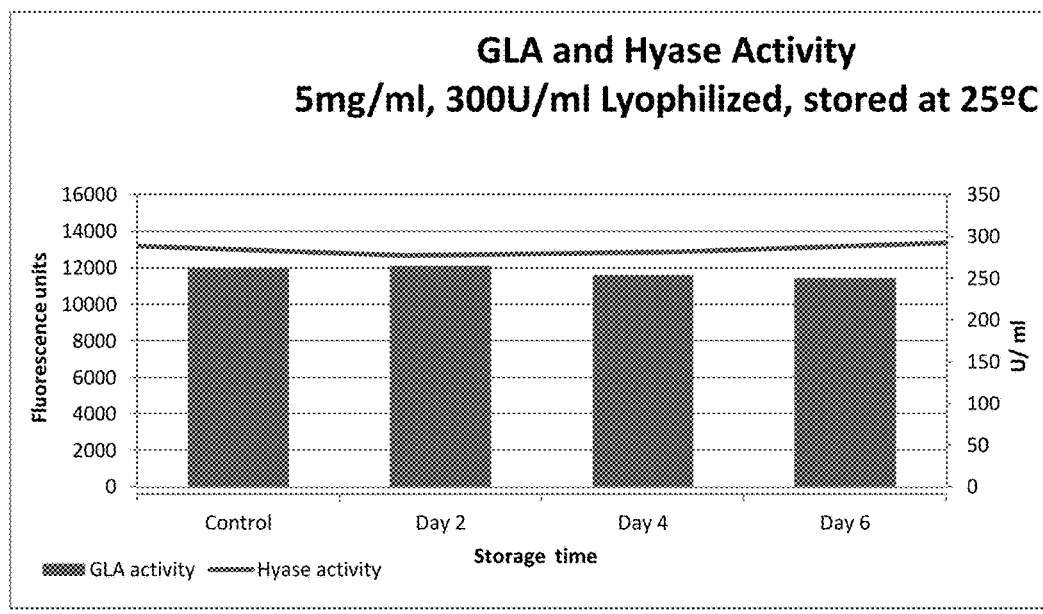
FIG. 7 illustrates GLA activity (bars) and Hyase activity (lines) of Formulation D (GLA 5 mg/ml, Hyaluronidase 300 U/ml, 6 mg/ml mannitol, sodium phosphate, pH 7; Lyophilized) on days 0 (control), 2, 4, and 6 during storage at 25° C.
Figure 8:
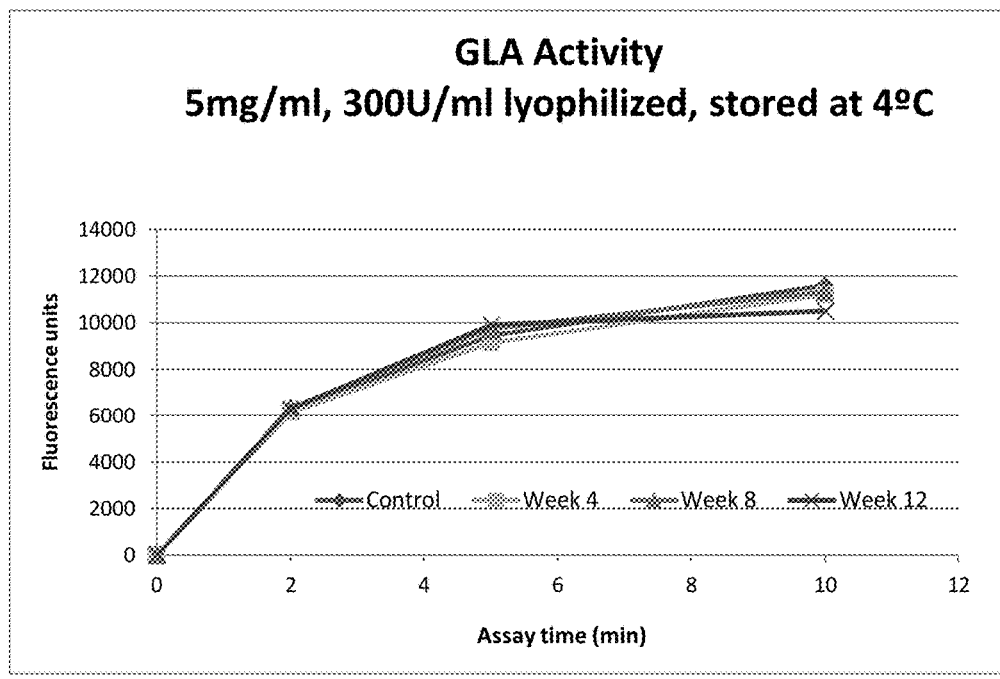
FIG. 8 illustrates GLA activity of Formulation D (GLA 5 mg/ml, Hyaluronidase 300 U/ml, 6 mg/ml mannitol, sodium phosphate, pH 7; Lyophilized) on weeks 0 (control), 4, 8, and 12 during storage at 4° C., following 0, 2, 4, 6, 8, or 10 minutes of fluorometric assay time.

Formulation D was a lyophilized preparation of GLA and bovine hyaluronidase in sodium phosphate buffer at concentrations of 5 mg/ml and 300 U/ml respectively. Polysorbate 20 at 0.23 mg/ml was added to the solution and adjusted to pH 7 with sodium hydroxide. Aliquots of 300 μl are lyophilized in Freezone Triad chamber system (Labconco, Kansas City, Mo.) and stored in 1.0 ml borosilicate glass vials at 4° C. for 12 weeks and at 25° C. for 6 days. Baseline control at 4° C. was assessed after overnight incubation and control for 25° C. was assayed immediately after formulation and lyophilization. All samples were reconstituted with purified water (EMD Millipore, Darmstadt, Germany) and diluted prior to assays. The stability and individual enzyme potency were determined according to the tables 10-12, and is illustrated in FIGS. 7-8.

TABLE 10

GLA and Hyase activity of Formulation D (GLA 5 mg/ml, Hyaluronidase 300 U/ml, 6 mg/ml mannitol, sodium phosphate, pH 7; Lyophilized) on weeks 0 (control), 4, 8, and 12 during storage at 4° C.

| Temperature | Storage time | GLA activity (FU t = 10) | % GLA activity | Hyase activity (U/ml) | % Hyase activity |
|---|---|---|---|---|---|
| 4 C. | Control (overnight storage) | 11608 | 100% | 292 | 100% |
| | Week 4 | 11216 | 97% | 295 | 101% |
| | Week 8 | 11324 | 98% | 294 | 101% |
| | Week 12 | 10492 | 90% | 287 | 98% |

TABLE 11

GLA and Hyase activity of Formulation D (GLA 5 mg/ml, Hyaluronidase 300 U/ml, 6 mg/ml mannitol, sodium phosphate, pH 7; Lyophilized) on days 0 (control), 2, 4, and 6 during storage at 25° C.

| | | GLA activity | % GLA activity | Hyase activity | % Hyase activity |
|---|---|---|---|---|---|
| 25 C. | Control (immediately after formulation/ lyophilization) | 11994 | 100% | 288 | 100% |
| | Day 2 | 12092 | 101% | 277 | 96% |
| | Day 4 | 11611 | 97% | 281 | 98% |
| | Day 6 | 11447 | 95% | 292 | 101% |

TABLE 12

GLA activity of Formulation D (GLA 5 mg/ml, Hyaluronidase 300 U/ml, 6 mg/ml mannitol, sodium phosphate, pH 7; Lyophilized) on weeks 0 (control), 4, 8, and 12 during storage at 4° C., following 0, 2, 5 or 10 minutes of fluorometric assay time.

| Time (min) | Control | Week 4 | Week 8 | Week 12 |
|---|---|---|---|---|
| 0 | 0 | 0 | 0 | 0 |
| 2 | 6258 | 6162 | 6344 | 6327 |
| 5 | 9456 | 9154 | 9735 | 9904 |
| 10 | 11608 | 11216 | 11324 | 10492 |

Example 12: Pre-Clinical Animal Study

Animals

A group of 10 jugular vein cannulated (JVC) Sprague-Dawley rats are obtained from Taconic Biosciences (Germantown, N.Y.) at ~6 weeks of age whereby 4 rats are selected for the experiments. Animals are divided evenly into subcutaneous and intravenous groups and housed individually with free access to food and water before and during the study. The remaining rats are used for control or as replacement subjects in the event of cannula or tube failure. All procedures comply with USDA and institutional guidelines regarding animal care and use.

Dosing

Subcutaneous administration is carried out on animals restrained in Decapicone bags (Braintree Scientific, Braintree, Mass.). A dosing needle tip is inserted beneath a scapular skin fold and the bolus dose is administered at a dosage of 1 mg/kg or ~0.25 ml per rat of the subcutaneous formulation containing radiolabeled ($^{125}$I) GLA and non-radiolabeled hyaluronidase. Intravenous administration is carried out using a 23-gauge aluminum hub blunt needle (Kendall Tyco Healthcare Mansfield, Mass.) attached to an individualized pre-filled syringe via the external catheter.

Serial Blood Collection

A 23-gauge needle attached to a 1 ml syringe is used to withdraw 0.25 ml (not to exceed 10% of total circulating volume per 24 hours) of blood via the external catheter during time points of 30 min, 1 h, 2 h, 3 h, 4 h, 8 hr, 12 hr, 24 hr, 36 h, and 48 h schedule for each group and flushed with 30 ul saline to prevent thrombosis. The blood sample is immediately transferred to a 0.4 ml serum separator microtainer tube (BD Scientific Franklin Lakes, N.J.) and centrifuged at 11,000 rpm (8500×g) for 2 min in room temperature. The serum is transferred to a 1.2 ml cryovial (Fisher Scientific, Chicago Ill.) and stored at −80 C for future analysis.

Tissue Sampling

Samples from injection-site skin, distal skin, testes, kidneys, spleen, liver, heart, lungs and thyroid are collected 12 h, 24 h, 36 h, and 48 h time points to assess the accumulation of GLA. Organs are harvested through dissection and are weighed and stored in 5 ml conical tubes (Fisher Scientific, Chicago Ill.) at 4° C. for immediate processing. A portion of the organ(s) is transferred and weighed in a standard radioimmunoassay (RIA) tube (PerkinElmer Boston, Mass.).

Gamma Counting

Tissue in RIA tubes are quantified using a WIZARD automatic gamma counter (PerkinElmer Boston, Mass.) to measure the disintegrations per minute (DPM) of each sample over 60 seconds. The DPM is converted to CPM using an internal efficiency algorithm with tissues from control rats as blank. Serum consisting of 100 ul serum aliquot of each sample is transferred to a RIA tube and quantified using a WIZARD automatic gamma counter (PerkinElmer Boston, Mass.) to measure CPM/ml. Serum from control rats is used as blank correction.

Data Analysis

Tissue radioactivity is quantified in CPM/mg and corrected with samples from control rats. Whole organ radioactivity of subcutaneous administration is expressed as a percent of total dose at each time point and subsequently compared to intravenous administration. Serum raw data is tabulated and non-compartmental analysis of radioactivity is performed on WinNonLin (Pharsight, Mountain View Calif.) to yield elimination half-life, $C_{max}$, $t_{max}$, AUC, and Vd.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition administered via subcutaneous or intradermal delivery to treat Fabry disease, the composition comprising:
   alpha-galactosidase A (GLA) in an amount between about 1 mg to about 5 mg; and
   hyaluronidase in an amount corresponding to about 10 U to about 300 U per single unit dose for facilitating subcutaneous or intradermal delivery of the GLA into a patient in need thereof, wherein the amount of hyaluronidase is limited to ensure that the GLA is delivered throughout the patient's body not including the patient's brain or bone,
   wherein the GLA is used to treat Fabry disease.

2. The composition of claim 1, wherein the stable formulation is aqueous and is stable for at least 3 months when stored at 2-8° C.

3. The composition of claim 1, wherein the stable formulation is lyophilized and is stable for at least 6 months when stored at 2-8° C.

4. The composition of claim 1, wherein the GLA maintains at least 50% of its activity during storage.

5. The composition of claim 1, wherein the GLA is a mammalian GLA.

6. The composition of claim 1 wherein the GLA is recombinant.

7. The composition of claim 1, wherein the hyaluronidase is in an amount corresponding to 50-100 U per single unit dose.

8. The composition of claim 1, wherein the hyaluronidase is animal-derived.

9. The composition of claim 1, wherein the hyaluronidase is recombinant.

10. The composition of claim 1, wherein the composition is packaged in a prefilled syringe.

11. The composition of claim 10, wherein syringe comprises a first chamber and a second chamber, wherein the first chamber comprises a lyophilized form of the composition, and the second chamber comprises a pharmaceutically acceptable diluent for reconstitution of the composition.

12. The composition of claim 1, wherein the composition is a multi-dose formulation.

13. The composition of claim 1, wherein the hyaluronidase is in an amount corresponding to 10-100 U per single unit dose.

14. The composition of claim 1, wherein the hyaluronidase is in an amount corresponding to 10-200 U-per single unit dose.

15. The composition of claim 1, wherein the hyaluronidase is bovine hyaluronidase.

16. The composition of claim 1, wherein the composition is formulated to give a $t_{max}$ of the GLA in a patient's bloodstream within 12 hours following administration of a single dose subcutaneous injection of the composition.

17. The composition of claim 1, further comprising an excipient selected from the group consisting of a buffering agent, a non-ionic surfactant, a stabilizer, a preservative and combinations thereof.

18. The composition of claim 17, wherein the buffering agent is selected from the group consisting of phosphate, histidine, citrate and combinations thereof.

19. The composition of claim 17, wherein the stabilizer is selected from the group consisting of mannitol, methionine, glycine, argeinine, albumin, trehalose, sucrose and combinations thereof.

20. The composition of claim 17, wherein the non-ionic surfactant is selected from the group consisting of polysorbate 20, polysorbate 80, poloxamer 188, polyethylene-polypropylene copolymer and combinations thereof, and wherein the stabilizer is selected from the group consisting of mannitol, methionine, glycine, argeinine, albumin, trehalose, sucrose and combinations thereof.

* * * * *